(12) United States Patent
Ott et al.

(10) Patent No.: US 7,250,035 B1
(45) Date of Patent: Jul. 31, 2007

(54) METHOD AND APPARATUS FOR TREATING GAS FOR DELIVERY TO AN ANIMAL

(75) Inventors: Douglas E. Ott, Macon, GA (US); John F. Schaefer, High Rolls, NM (US); Robert I. Gray, Macon, GA (US)

(73) Assignee: Lexion Medical, LLC, St. Paul, MN (US)

( * ) Notice: Subject to any disclaimer, the term of this patent is extended or adjusted under 35 U.S.C. 154(b) by 0 days.

(21) Appl. No.: 09/363,234

(22) Filed: Jul. 27, 1999

Related U.S. Application Data

(63) Continuation-in-part of application No. 09/081,186, filed on May 19, 1998, now Pat. No. 6,068,609.

(51) Int. Cl.
*A61M 37/00* (2006.01)

(52) U.S. Cl. ....................................... 604/26

(58) Field of Classification Search ............ 604/23–24, 604/26; 261/129, 142; 236/44
See application file for complete search history.

(56) References Cited

U.S. PATENT DOCUMENTS

| | | | |
|---|---|---|---|
| 2,408,136 A | 9/1946 | Fox | |
| 3,582,717 A | 6/1971 | Perlaky | |
| 3,871,371 A | 3/1975 | Weigl | 128/145.8 |
| 4,092,635 A | 5/1978 | Warner | |
| 4,121,583 A | 10/1978 | Chen | 128/212 |
| 4,215,681 A | 8/1980 | Zalkin et al. | |
| 4,276,128 A * | 6/1981 | Nishino et al. | 205/200 |
| 4,303,601 A | 12/1981 | Grimm et al. | |
| 4,360,017 A | 11/1982 | Barlett | |
| 4,369,777 A | 1/1983 | Lwoff et al. | |
| 4,401,114 A | 8/1983 | Lwoff et al. | |
| 4,621,632 A * | 11/1986 | Bartels et al. | 128/203.27 |
| 4,621,633 A | 11/1986 | Bowles et al. | 128/203.17 |
| 4,674,494 A | 6/1987 | Wiencek | |
| 4,770,168 A * | 9/1988 | Rusz et al. | 128/203.12 |
| 4,825,863 A | 5/1989 | Dittmar et al. | 128/203.27 |
| 5,006,109 A | 4/1991 | Douglas et al. | |
| 5,013,294 A | 5/1991 | Baier | |
| 5,062,145 A | 10/1991 | Zwaan et al. | |
| 5,098,375 A | 3/1992 | Baier | |
| 5,139,478 A | 8/1992 | Koninckx et al. | 604/26 |
| 5,148,801 A | 9/1992 | Douwens et al. | 128/203.16 |

(Continued)

FOREIGN PATENT DOCUMENTS

DE 28 34 622 2/1979

(Continued)

OTHER PUBLICATIONS

PCT Search Report, PCT/US00/13717.

(Continued)

*Primary Examiner*—Manuel Mendez
(74) *Attorney, Agent, or Firm*—Marshall & Melhorn, LLC

(57) ABSTRACT

A method and apparatus for treating gas for delivery into a body cavity, body space or body surface of an animal. The apparatus comprises a housing defining a chamber having an entry port and an exit port. One or more agents are released into the gas stream that flows through the chamber so that the gas stream carries the agent to the animal.

29 Claims, 10 Drawing Sheets

U.S. PATENT DOCUMENTS

| | | | | |
|---|---|---|---|---|
| 5,246,419 A * | 9/1993 | Absten | ............................ | 604/26 |
| 5,411,474 A * | 5/1995 | Ott et al. | ............................ | 604/26 |
| 5,482,031 A | 1/1996 | Lambert | | |
| 6,010,118 A | 1/2000 | Milewicz | | |
| 6,014,890 A | 1/2000 | Breen | | |
| 6,039,696 A | 3/2000 | Bell | | |
| 6,050,260 A * | 4/2000 | Daniell et al. | ............ | 128/204.22 |
| 6,814,714 B1 | 11/2004 | Novak et al. | | |
| 2002/0072700 A1 | 6/2002 | Mantell et al. | | |

FOREIGN PATENT DOCUMENTS

| | | |
|---|---|---|
| DE | 28 10 325 A1 | 9/1979 |
| DE | 31 39 135 A1 | 10/1982 |
| DE | 34 30 541 A1 | 7/1985 |
| DE | 36 15 611 C2 | 11/1986 |
| DE | 39 32 766 A1 | 4/1990 |
| DE | 39 27 594 A1 | 6/1990 |
| DE | 195 10 710 A1 | 3/1995 |
| DE | 195 10 710 A1 | 9/1996 |
| EP | 0 169 151 B1 | 1/1986 |
| EP | 0 569 241 A2 | 6/1993 |
| EP | 0 387 220 B2 | 1/1995 |
| EP | 0 533 644 B1 | 12/1996 |
| WO | WO 94/28952 | 12/1994 |
| WO | WO 98/26826 | 6/1998 |

OTHER PUBLICATIONS

Laparoscopic Hypothermia, by Douglas E. Ott, published in *Journal of Laparoendoscopic Surgery*, vol. 1, No. 3, 1991, pp. 127-131.

Correction of Laparoscopic Insufflation Hypothermia, by Douglas E. Ott, published in *Journal of Laparoendoscopic Surgery*, vol. 1, No. 4, 1991, pp. 183-186.

Contamination via Gynecologic Endoscopy, by Douglas E. Ott, published in *Journal of Gynecologic Surgery*, vol. 5, 1989, pp. 205-208.

Moisture-conserving efficiency of condenser humidifiers, by Ogino et al., published in *Anaesthesia*, vol. 40, 1985, pp. 990-995.

The Liquid Barrier Filter—A New Concept To Eliminate Particulate Contaminants From Gases, by Seufert et al., published in *Health Physics*, vol. 42, No. 2, 1982, pp. 209-216.

Humidification of Rapidly Flowing Gas, by Poulton et al., published in *Critical Care Medicine*, vol. 9, No. 1, 1981, pp. 59-63.

Temperature Alarm And Cut-Out System For Use With Heated Water Humidifiers, by Whitehurst et al., published in *British Journal of Anaesthesia*, vol. 52, 1980, pp. 557-558.

Humidification in a Modified Circle System, by Chalon et al., published in *Anesthesia And Analgesia*, vol. 56, No. 3, May-Jun. 1979, pp. 216-220.

A New Humidifier, by Grant et al., published in *Anaesthesia and Intensive Care*, vol. IV, No. 3, Aug, 1976, pp. 205-210.

A Safe Nonrebreathing System: Humidity, Sterility, Cost, by Dolorico et al., published in *Anesthesia And Analgesia*, vol. 53, No. 1, Jan.-Feb. 1974, pp. 75-79.

Hypothermia Induced by Laparoscopic Insufflation, by Bessell et al., published in *Surgical Endoscopy*, vol. 9, 1995, pp. 791-796.

Pain Intensity Following Laparoscopy, by Korell et al., published in *Surgical Laparoscopy & Endoscopy*, vol. 6, 1996, pp. 375-379.

Influence of Gas Temperature During Laparoscopic Procedures, J.R. Bessell & G.J. Maddern, published in *The Pathophysiology of Pneumo-peritoneum*, Rosenthal et al., Springer, 1998, pp. 18-27.

*Cook Medical Technology Technological Observer*, Cook Australia, Jan. 1998, pp. 1-5.

European Supplementary Partial Search Report, Aug. 3, 2004.

M.A. Reymond et al., Feasibility of Therapeutic Pneumoperitoneum in a Large Animal Model Using a Microvaporisator; *Surgial Endoscopy—Ultrasound and Interventional Techniques*, Springer-Verlag, 2000, pp. 51-55.

Koninckx & Vandermeersch, The Persufflator: An insufflation device for laparoscopy and especially for $CO_2$-mlaser-endoscopic surgery, Human Reproduction, vol. 6, No. 9, pp. 1288-1290.

Karrer, W., *Pillars of therapy of chronic obstructive bronchitis*, Schweiz Rundsch Med. Prax. Feb. 7, 1989; 78(6):121-5, Germany.

Siede & Schneider, *Handbook and Atlas of Laparoscopy*, pub. J.F. Lehmanns Verlag, Munich, Germany, 1962, pp. 19-20. & English Translation.

Supplementary Search Report, May 4, 2004.

PCT Search Report, PCT/US00/13717, (1999).

Lexion Medical, LLC v. Northgate Technologies, Inc., Smith & Nephew, Inc. and Linvatec Corporation, Order, 1:04-CV-5705, in the United States District Court for the Northern District of Illinois Eastern Division, (2007).

* cited by examiner

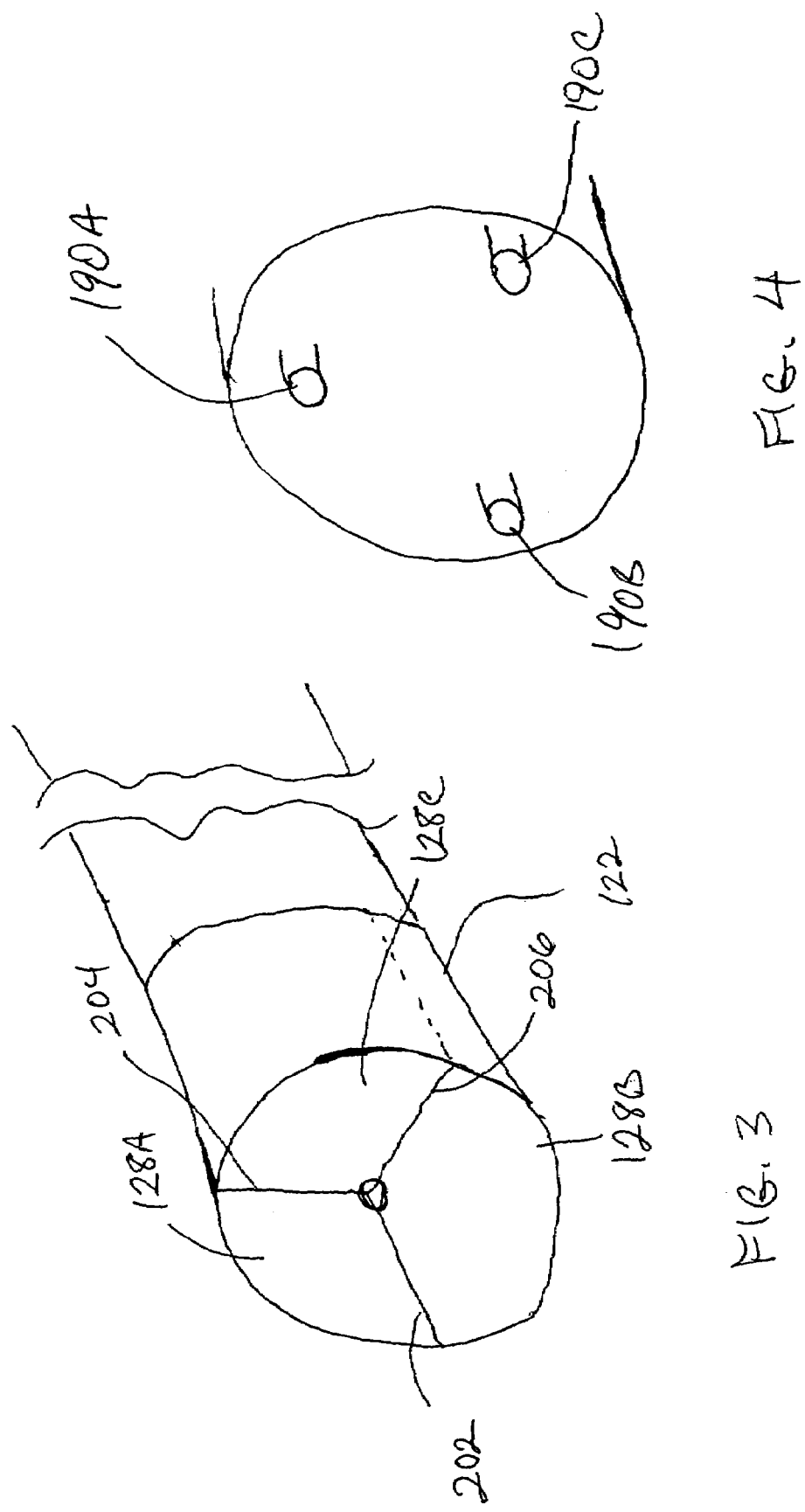

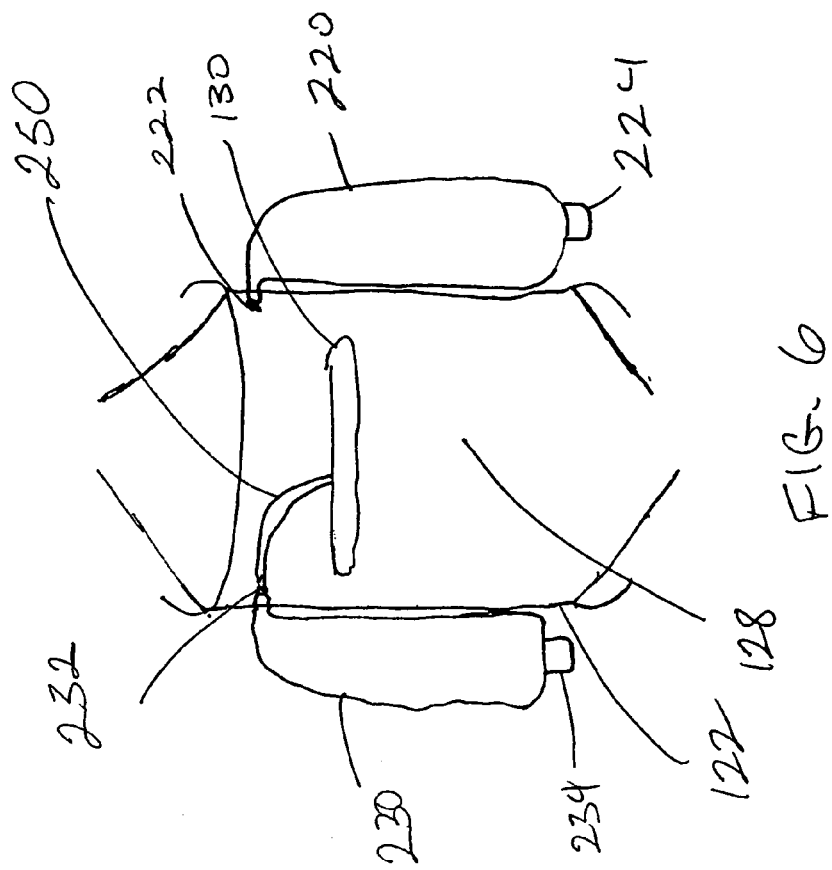
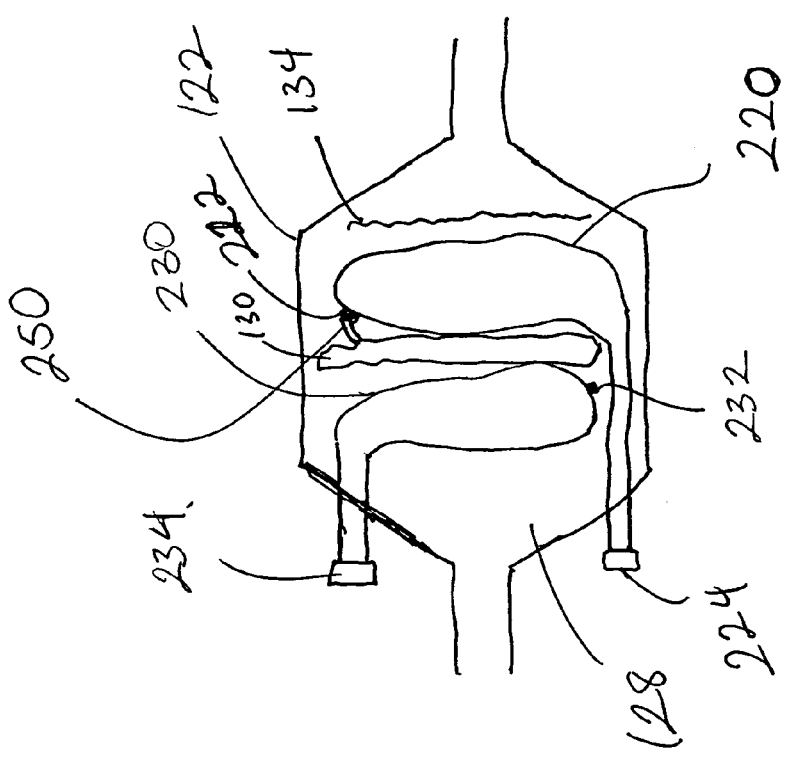

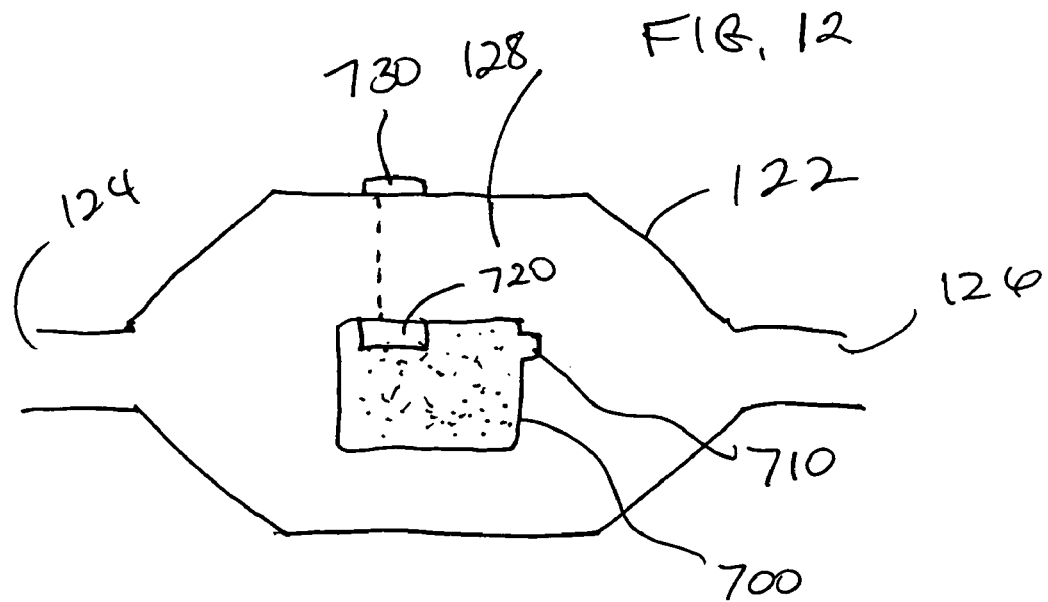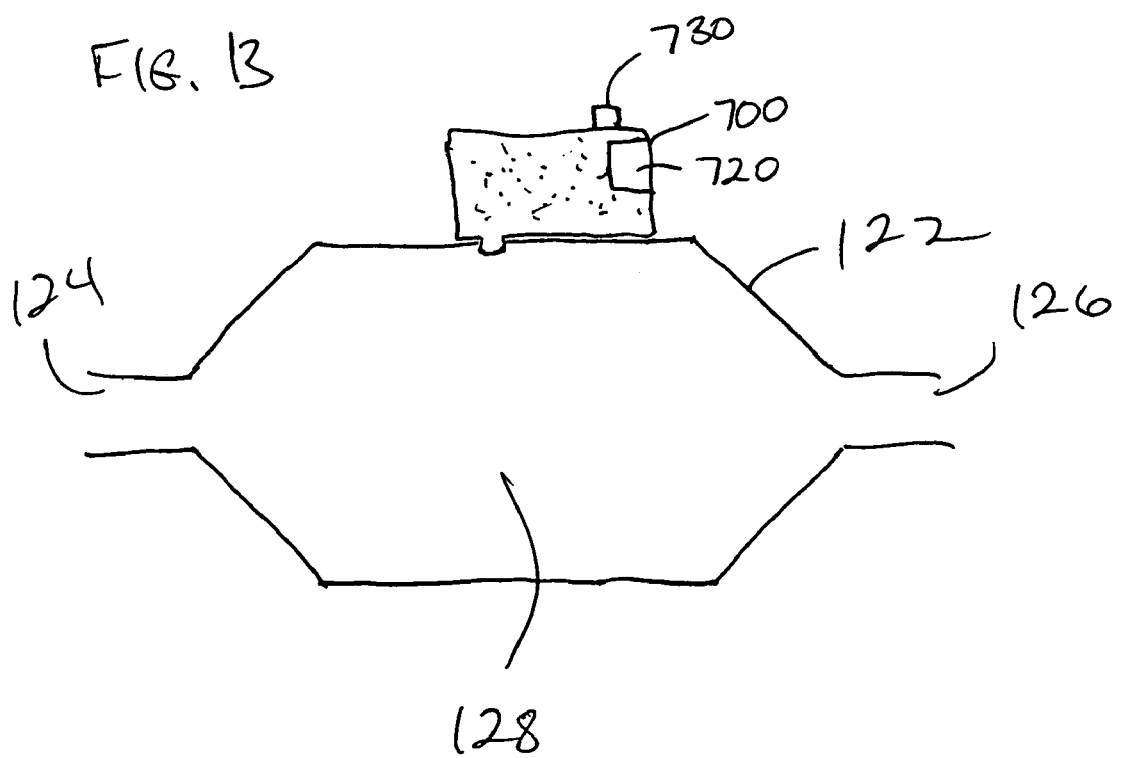

METHOD AND APPARATUS FOR TREATING GAS FOR DELIVERY TO AN ANIMAL

RELATED APPLICATION

This application is continuation-in-part of U.S. application Ser. No. 09/081,186, filed May 19, 1998 now U.S. Pat. No. 6,068,609, entitled "Method and Apparatus for Conditioning Gas for Medical Procedures Having Humidity Monitoring and Recharge Alert," the entirety of which is incorporated herein by reference.

BACKGROUND OF THE INVENTION

1. Field of the Invention

This invention relates to treating gases delivered into body cavities, spaces or body surfaces of an animal. More specifically, it relates to a device for, and method of, treating gases with one or more agents to be carried by the gas stream to an animal.

2. Related Art

The delivery of gas into the body of a patient is well known for many purposes. Gas is delivered into a body cavity, such as the abdomen, to distend a compliant surface or create pressure for a specific purpose. Distention of the abdomen using gas creates a pneumoperitoneum that achieves a space in which one can examine, repair, remove and surgically manipulate. The space created by gas insufflation is a basic component of laparoscopic surgery. Within the space of the body created by the gas flow and pressure, tissue surfaces and organs can be visualized safely and instruments placed that are used for diagnostic and therapeutic purposes. Examples of such uses include, but are not limited to, coagulation, incision, grasping, clamping, suturing, stapling, moving, retracting and morcelizing. The quality of the gas stream can be modified and conditioned by filtering, heating and hydrating. U.S. Pat. No. 5,411,474 and the aforementioned U.S. patent application disclose methods for conditioning gas in this manner.

There is room for further improvement and advancement. During a procedure that instills gas to a body cavity, body space or body surface, the addition of pharmacologically active or inert materials (organic or inorganic) can enhance tissue healing, reduce infection, reduce adhesion formation, modify the immunologic response, treat specific disease processes, reduce pain and assist in diagnosis. It is desirable to provide an apparatus and method suitable for treating gas in such a manner.

SUMMARY OF THE INVENTION

Briefly, the present invention is directed to a method and apparatus for treating gas with one or more agents for delivery to a body cavity, body space or body surface. The gas is received into the apparatus from a gas source. The apparatus comprises a housing defining at least one chamber having an entry port and an exit port, the entry port for receiving a gas stream from a gas source. A quantity of one or more agents is released into the chamber to be admixed in the gas stream that is delivered to the animal by a delivery device. The gas stream is optionally humidified and/or heated in the housing.

The above and other objects and advantages of the present invention will become more readily apparent when reference is made to the following description taken in conjunction with the accompanying drawings.

BRIEF DESCRIPTION OF THE DRAWINGS

FIG. 3 is a perspective view of a portion of the gas treater housing according to an embodiment of the present invention comprising a plurality of distinct chambers.

FIG. 4 is an end view of the gas treater housing according to the embodiment of FIG. 3.

FIG. 5 is an internal view of the gas treater housing according to another embodiment featuring one or more bag members inside the housing.

FIG. 6 is an internal view of the gas treater housing according to still another embodiment featuring one or more bag members outside the housing.

FIG. 12 is an internal view of a gas treater housing showing a container for releasing a quantity of a solid phase agent into the chamber.

FIG. 13 is an view of a gas treater housing, similar to FIG. 12, but showing the container positioned outside of the chamber.

DETAILED DESCRIPTION OF THE PREFERRED EMBODIMENTS

Definitions

Figure 1:
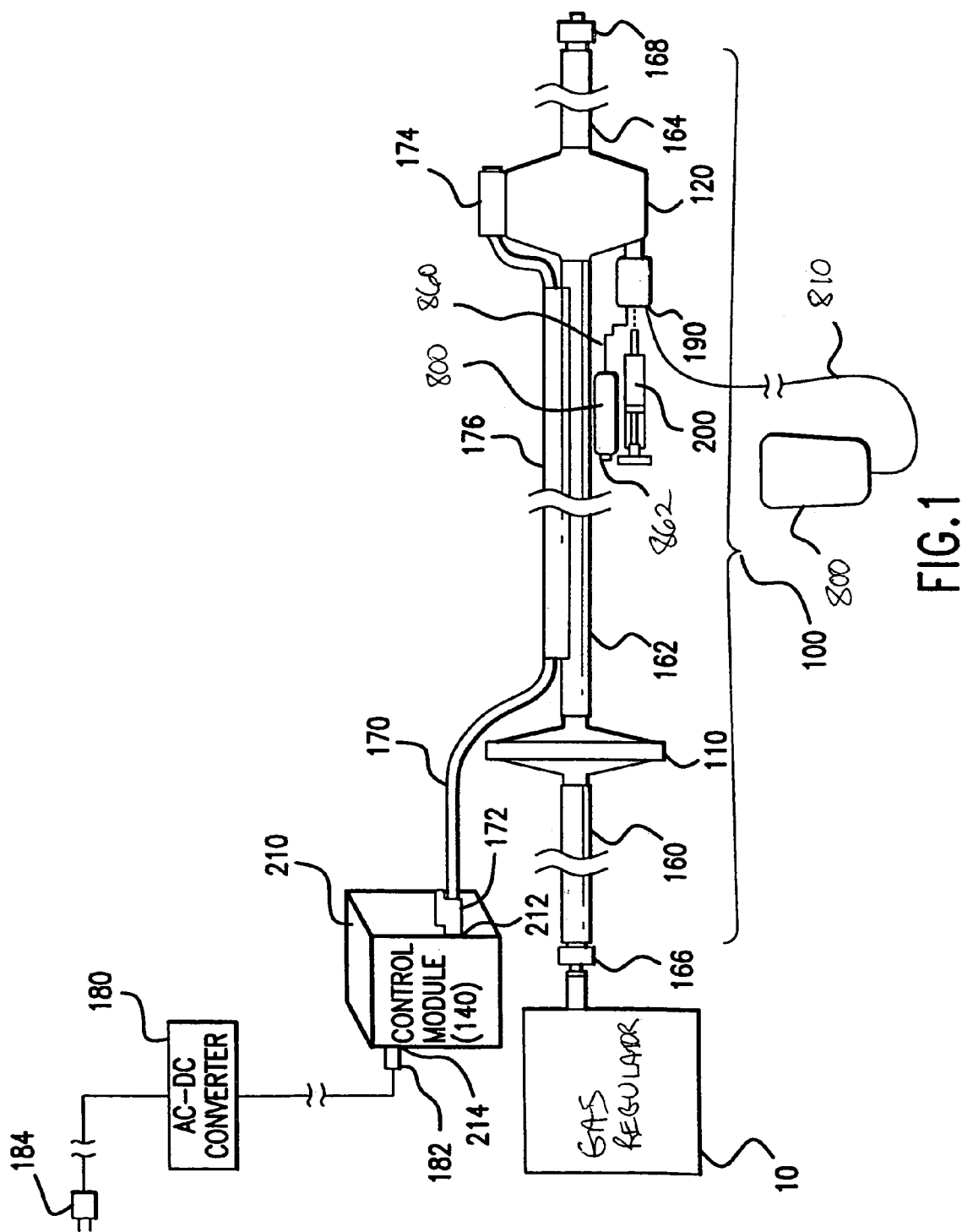
FIG. 1 is a schematic view of an apparatus according to the present invention.

As used herein, "a predetermined temperature" or "a predetermined temperature range" is one that has been preset or programmed by the user during a procedure. For example a desirable temperature range may be physiological body temperature, i.e., approximately 35-40° C. As explained hereinafter, the temperature of the gas may be adjusted by a "dial" type or other similar adjustment.

As used herein, the term "humidifying solution" means water, normal saline, lactated Ringers, any buffered or unbuffered liquid or solution, an aqueous solution, a non-water based solution, a combination of water or non-water solutions and other substances, or a gel substance containing water or non-water solutions and other substances.

As used herein, the term "agent" means any organic substance, inorganic substance, inert or biologically active substance or pharmacologic material, that may effect or enhance tissue healing, reduce infection, reduce adhesions formation, modify the immunologic response, treat specific disease processes, reduce pain or be used for any therapeutic or diagnostic purpose. This includes materials in solid, liquid or gas phase, and materials that are water (aqueous) based, colloid and non-colloid suspensions, mixtures, solutions, hydrogels, lypholized materials, hydrophobic, hydrophilic, anionic, cationic, surface active agents, surgical adjuvants, anticoagulants, antibiotics, immunologic stimulators, immunologic suppressants, growth inhibitors, grow stimulators, diagnostic materials, anesthetic agents, analgesic agents, and materials by themselves or dissolved or based in other materials, such as, but not limited to, alcohols, ethers, esters, lipids and solvents. The agent can be dry, such as in a powder form. Any material that can be carried by the flow of gas into a body cavity or onto a surface for therapeutic or diagnostic purposes can be delivered in accordance with this invention. It is not intended to limit the present invention to the above examples of agents. Furthermore, the gas stream may be treated with any type or combination of agents in accordance with the present invention. An example is to treat the gas stream with a humidifying solution for hydration to prevent dessication, an antibiotic to reduce infection, an anti-inflammatory to reduce inflammation and an anti-adhesive to reduce adhesions and improve healing. Agents such as those sold under the trademarks Adept manufactured by ML Laboratories, Adcon manufactured by Gliatech and Atrisol manufactured by Atrix Laboratories can be used to reduce adhesions.

As used herein, the term "gas" includes any gas or combination or mixture of gases in any proportion that occurs naturally or can be manufactured or placed or created in a container.

The term "treating" used in connection with treating of the gas stream means to inject or release one or more agents into the gas stream so that the gas stream is a fume or dust in the case of a solid phase agent, or a mist or spray in the case of a liquid phase agent. In some embodiments, such as where the agent is in liquid form, the agent is wicked off or dislodged from a container. In other cases, the agent is injected or released into the gas stream. In general, the gas stream to be treated with one or more agents is also humidified.

The terms "cavity" or "space" mean any body cavity or space including the abdomen, plural cavity, knee space, shoulder space, eye ball, stomach and lung.

The basic tenet of the present invention is to treat a flowing gas stream with one or more agents so that the agent(s) actively or passively are injected into the gas stream and are made part of the gas stream as a result of the dynamics of flow, vapor pressure and/or rate of evaporation. The gas stream thereby is modified to contain additives that are determined desirable by the user for purposes of enhancing the outcome of a gas delivery event in connection with, for example, a particular treatment or diagnostic procedure.

The term "body surface" means any surface of the body, whether internal or external, and whether exposed naturally or by way of surgical procedure.

Referring to FIG. 1, the apparatus for treating or conditioning gas is shown generally at reference numeral 100. The apparatus 100 is adapted to receive gas from a gas regulator 10 (high or low pressure, high or low flow rate), such as an insufflator. The apparatus comprises a gas treater 120, an optional filter 110 and an optional control module 140. Tubes are provided to connect the various components of the apparatus together. Specifically, a first tube segment 160 connects the outlet of the gas regulator 10 to the inlet tubing of the filter 110 via a male Luer lock 166 or any appropriate adapter compatible with the insufflator outlet port. A second tube segment 162 connects the outlet of the filter 110 to the inlet of the gas treater 120. A third tube segment 164 connects the outlet of the gas treater 120 by a male Luer lock 168 (or other appropriate fitting adapter) to a gas delivery device (not shown), such as a trocar, verres needle, endoscope or a tube that enters a body cavity or space that delivers the treated gas into the body of a animal. Alternatively, if the gas is to be delivered to a body surface, the gas delivery device may be shaped, formed or otherwise configured to direct or spread the flow of gas onto a surface.

The tubing of the tube segments 160, 162 and 164 is preferably flexible and sufficiently long to permit the gas regulator 10 and control module 140 to be placed at a convenient distance from a animal undergoing procedure requiring gas delivery. For applications of the apparatus 100 where the temperature of the gas stream should be within a desired range when delivered, the gas treater 120 is preferably placed immediately adjacent to that location where the gas is to be delivered.

The filter 110 is an optional element and consists of a high efficiency, hydrophobic filter (for example, Gelman Sciences Metricel M5PU025) having a pore size preferably small enough to exclude all solid particles and bacterial or fungal agents that may have been generated in a gas supply cylinder or the gas regulator 10 (i.e., 0.5 micron or less and preferably about 0.3 micron). A preferable filter is a hydrophobic filter, such as a glass fiber-type filter, e.g., Metrigard by Gelman Sciences or Porous Media Ultraphobic filter, model DDDF 4700 M02K-GB. Other suitable filters include polysulfone (SupQr, HT Tuffrin, Gelman Sciences) and mixed cellulose esters (GN-6 Metricel, Gelman Sciences), for example. Decreasing the pore size of filter 110 below 0.1 micron causes a concomitant increase in pressure drop of gas, and thus flow rate is reduced significantly. If the procedure to be performed requires a relatively high pressure and/or flow rate of gas to the animal, such as laparoscopy, the pore size should preferably not decrease below 0.2 micron. A hydrophobic filter is preferable to a hydrophilic one, as a hydrophobic filter is less likely to tear under water pressure caused by accidentally suctioning or syphoning peritoneal or irrigation fluids.

In some applications, it is desirable that the gas treater 120 be connected immediately adjacent to a gas delivery device so that the gas travels a minimum distance from the outlet of the gas treater 120 to the conduit or connection to the interior of a animal. The purpose of this arrangement is to allow gas to be delivered to the animal while still at a temperature and water content or within a temperature range sufficiently close to the physiological interior body temperature or other body surface. That is, for some applications, the apparatus according to the invention prevents thermodynamic cooling of gases in transit to the animal, because it provides a highly efficient treatment chamber that, as a result of its efficiency, can be quite compact and thus be positioned very near to the animal.

The control module 140 is contained within an electrical housing 210 and is connected to the gas treater 120 by several wire pairs contained within an insulated electrical cable 170. In particular, the cable 170 has a connector 172 at one end that electrically connects into a circuit connector 212 of the housing 210 for the control module 140, and at the other end it is electrically connected to the gas treater 120 by a sealed electrical feedthrough 174. The cable 170 is attached to the tube segment 162 by a plastic tape or clip 176. Alternatively, the cable 170 is attached to the tube segment 162 by heat seal, extrusion, ultrasonic welding, glue or is passed through the interior of tube segment 162.

The control module 140 and associated components in the gas treater 120 are preferably powered by an AC-DC converter 180. The AC-DC converter 180 has an output that is connected by a plug connector 182 into a power receptacle 214 of the circuit within the control module 140, and has a standard AC wall outlet plug 184 that can be plugged into standard AC power outlets. For example, the AC-DC converter 180 is plugged into an AC power strip that is provided on other equipment in an operating room. Alternatively, electrical power for the apparatus is provided by a battery or photovoltaic source. Another alternative is to provide circuitry in the control module 140 that operates on AC signals, as opposed to DC signals, in which case the control module 140 could be powered directly by an AC outlet. The control module 140 and the heating and hydrating components inside the gas treater 120 will be described in more detail hereinafter.

In some embodiments, the gas treater 120 has a charging port 190 that is capable of receiving a supply of an agent and/or humidifying solution. For example, a syringe 200 containing a predetermined volume of liquid-based agent is introduced into the charging port 190 to inject it into the gas treater 120 for an initial charge or re-charge thereof. The apparatus 100 may be sold with the gas treater 120 pre-charged with a supply of an agent and/or humidifying solution such that an initial charge is not required for operation.

Figure 2:
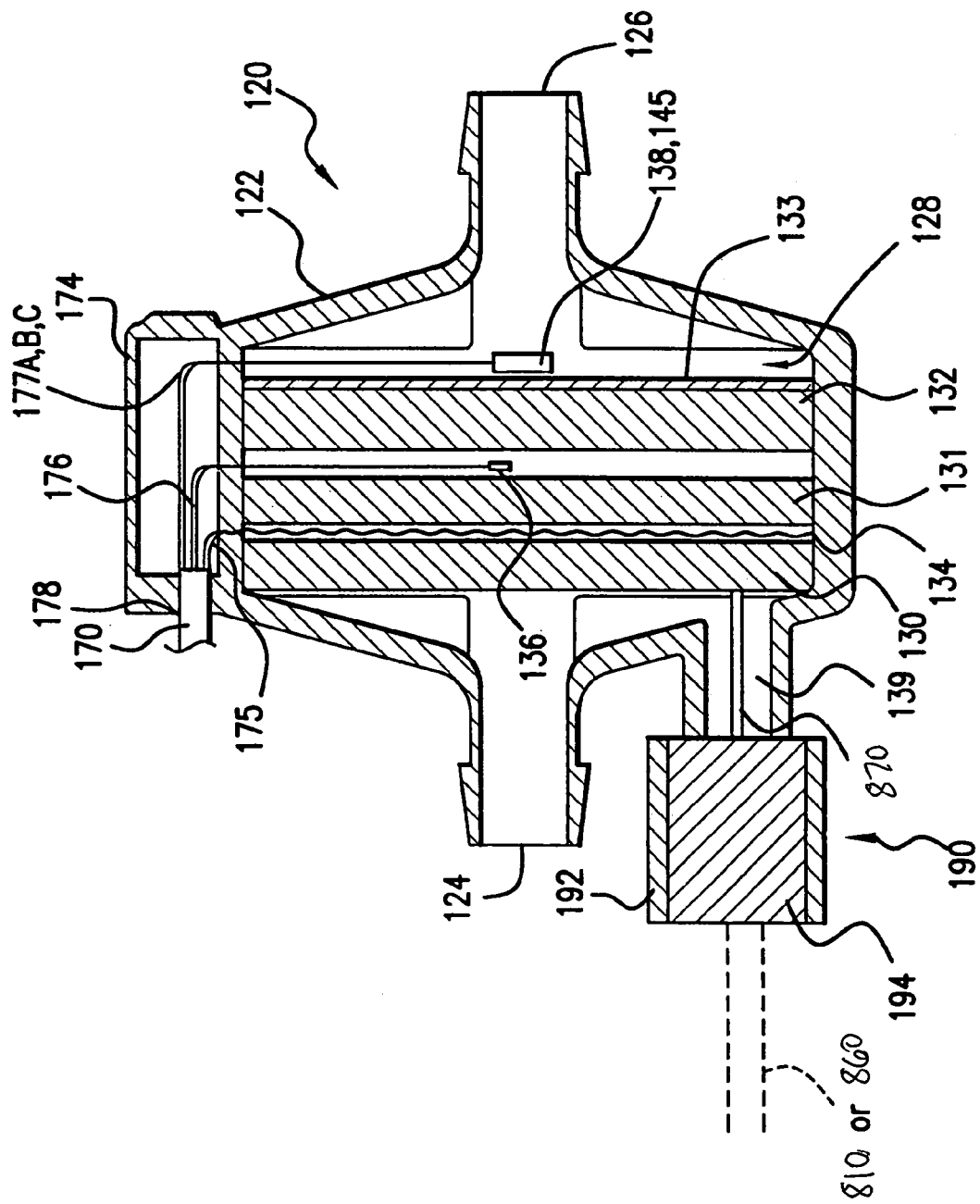
FIG. 2 is a cross-sectional view of the gas treater of the apparatus according to the present invention.

Turning to FIG. 2, the gas treater 120 will be described in greater detail. The gas treater 120 comprises a housing 122 having an (entry port) gas inlet 124 and an (exit port) gas outlet 126. The housing 122 defines a chamber 128 that contains a treatment subchamber for treating the gas supplied through the inlet with an agent, and in some embodiments, contains elements for substantially simultaneously heating and hydrating (humidifying), as well as means 136 for sensing the temperature of the gas and means 138 for sensing the relative humidity of the gas as it exits the chamber 128.

Specifically, in the embodiment of FIG. 2, within the chamber 128, there is provided a subchamber that comprises one or more layers of liquid-retaining or absorbing padding or sponge material, shown at reference numerals 130, 131 and 132. It should be understood that the number, spacing and absorbency of the liquid-retaining layers 130, 131 and 132 varies according to specific applications. Three layers are shown as an example. The material of the layers 130, 131 and 132 can be any desirable liquid-retaining or absorbent material, such as a rayon/polyester formed fabric (e.g., NU GAUZE™, manufactured and sold by Johnson & Johnson Medical, Inc.). The pore size of the selected material should be chosen according to a balance of liquid-retaining capabilities and low pressure drop considerations. The larger the pore size, the greater the liquid retention capability for gas contact for aerosolizing the gas.

Other forms of the treatment subchamber may consist of a subcontainer or subchamber of liquid within the chamber 128 (without absorbent layers) having a semi-permeable membrane on opposite ends to allow gas to pass therethrough. The agent in the chamber is optionally heated by a heating jacket placed around the chamber.

The heating means in the gas treater 120 consists of at least one heating element 134 positioned in the housing, such as between the absorbent layers 130 and 131. The heating element 134 is an electrically resistive wire, for example. The heating element 134 is placed preferably between absorbent layers or en-meshed within the layers of material (in the fabric). The heating element 134 heats the gas supplied through the inlet, under control of a heat control signal supplied by the control module 140, substantially simultaneous with the treatment of the gas as the gas passes through the chamber 128. Additional heating elements may be disposed within the chamber.

In order to sense the temperature and humidity of the gas as it exits the gas treater 120, a temperature sensor 136 and a relative humidity sensor 138 are provided. The temperature sensor 136 may be provided anywhere within the flow of gas in the chamber 128, but is preferably positioned on the downstream side of the heating element 134 between liquid-retaining layers. The temperature sensor 136 is a thermistor (for example, Thermometrics MA100 Series chip thermistor, or Thermometrics Series BR23, Thermometrics, Inc., Edison, N.J.). It is preferable that the temperature sensor 136 be accurate to within about 0.2° C. In the present invention, the temperature of the gas is preferably sensed after the gas has been treated (and optionally humidified) so that any change in the temperature of the gas as it is treated is corrected at that point in the apparatus, thereby compensating for enthalpy changes.

The humidity sensor 138 is positioned in the flow path of gas exiting the chamber 128, preferably downstream from the heating element 134 either between liquid-retaining layers or on the downstream side of the absorbent layers, proximate the exit port 126 of the housing 122. The humidity sensor 138 is preferably not in contact with a layer. FIG. 2 shows the humidity sensor 138 distal to the absorbent layers, separated from the liquid-retaining layer 132 by a porous mesh (plastic or metal) layer 133 that extends across the interior of the housing 122. The humidity sensor 138 actually is generally not in contact the porous mesh layer 133, but is spaced therefrom as well. The humidity sensor 138 is, in one embodiment, a humidity-sensitive capacitor sensor, such as a capacitive humidity sensor manufactured by Philips Corporation, which changes capacitance in response to humidity changes. The humidity sensor 138 measures the relative humidity of the gas as it passes through the chamber 128 to enable monitoring of the gas humidity, and in order to provide an indication of the amount of humidifying solution remaining in the gas treater 120, i.e., in layers 130, 131 and 132. As will be explained hereinafter, in one embodiment, a timer/divider integrated circuit (IC) 145 (FIG. 5), is connected to the humidity sensor 138 and is preferably disposed within the housing 122 together and substantially co-located with the humidity sensor 138.

One way to treat a gas stream with one or more agents using the embodiment of the gas treater 120 shown in FIG. 2 is to inject from a syringe 200 a liquid-based agent into the chamber 128 through the charging port 190 for absorption onto one of the layers 130-132. When the gas stream flows over the layers 130-132, the gas stream will become treated with agent and thereby carry the agent out of the gas treater 120 into a animal. Depending on the dimensions and type of absorbent pad or pads used, there is a capacity to the amount of agent that can be introduced into the chamber 128. The size of the chamber 128 can be increased to allow for larger pads, and therefore greater capacity.

Several additional embodiments of the invention will now be described in conjunction with FIGS. 3-9, and 12-15. In these embodiments, other configurations of the housing 122 of the gas treater 120 are described that are useful to treat the gas stream flowing through the gas treater housing 122 with one or more agents. These embodiments show different types of containers for containing an agent and releasing it into the gas stream in a chamber of the gas treater 120.

FIGS. 3 and 4 illustrate an embodiment for the gas treater housing 122 featuring multiple chambers, for example, three chambers 128A, 128B and 128C that extend a certain length portion (not necessarily all) of the housing 122. These chambers are separated by walls or partitions 202, 204 and 206. Associated with each chamber 128A, 128B and 128C is a charging port 190A, 190B and 190C, respectively to receive a supply of agent from a respective source, such as an external bag, syringe, etc. The agent is delivered under pressure into a chamber through its respective charging port, or is wicked off from a small opening of a bag (FIGS. 5 and 6) placed through the charging port into a chamber. Alternatively, within each chamber 128A, 128B and 128C is one or more absorbent pads or layers similar to that shown in FIG. 2, onto which a quantity of an agent is absorbed. Still a further alternative is to provide a separate semi-permeable membrane in each chamber filled with a different agent.

Each of the chambers can be charged with a different agent. For example, chamber 128A may be charged with a humidifying solution, chamber 128B may be charged with agent A and chamber 128C may be charged with agent B. Though not shown in FIGS. 3 and 4, it should be understood that the heating elements, temperature sensor and humidity sensor shown in FIG. 2 may optionally be included in their various configurations in the embodiment of the housing shown in FIGS. 3 and 4. In the embodiment of FIGS. 3 and 4, when the gas stream flows through the housing 122, the gas stream wicks off or dislodges the humidifying solution from chamber 128A, is mixed with agent A from chamber 128B and is mixed with agent B from chamber 128C. Thus, the gas stream that exits the housing 120 is hydrated and treated with the agents, for delivery to an animal.

FIGS. 5 and 6 illustrate another embodiment where the agents to be carried by the gas stream are contained within bags. In FIG. 5, there are, for example, two bags 220 and 230 each of which are to contain a quantity of an agent. The apparatus may be shipped with the bags 220 and 230 pre-loaded or pre-charged with a quantity of agents, or they may be filled with a quantity of agents prior to use. The bags 220 and 230 are formed of flexible material such as, polyethylene or other similar material. In one configuration, the bags 220 and 230 are formed of a semi-permeable membrane material such that the agent contained therein can be wicked off by the flowing gas stream over the surface of the bags through the housing 122. In another configuration, at the end of each bag 220 and 230 inside the housing 122 is a restrictive orifice, nozzle or hole 222 and 232, respectively, such as a spray hole or atomizer hole to allow for contact with the gas stream to be admixed therewith. At the other end of each bag 220 and 230 is an optional charging port 224 and 234, respectively, to allow the introduction of a quantity of an agent into the bags 220 and 230. Openings are made in the housing 122 to allow a length of the bags 220 and 230 to pass therethrough and into the chamber.

As the bags are filled, they expand inside the chamber 128. The pressure of the quantity of agent in the bags 220 and 230 and/or capillary action at the holes 222 and 232 forces the agent to drip out of the holes 222 and 232 to be wicked off or dislodged by the flowing gas stream through the chamber 128 and carried out of the exit port of the housing 122. In the configuration where the bags 220 and 230 are formed of a semi-permeable membrane material, the pressure of the quantity of agent in the bags facilitates the wicking off of the agent through the membrane. The bags 220 and 230 are deployed within the chamber 128 so that when they are filled, they expand and are substantially confined to a predetermined region of the chamber so as not to interfere with gas flow over the other bag. For example, a heating coil 124 or an absorbent pad can be used to separate the bags 220 and 230 in the chamber 128.

FIG. 5 shows only two bags 220 and 230, but it should be understood that one or any number of bags may be suitable depending on the number of agents to be carried by the gas stream.

FIG. 6 shows a variation of the embodiment of FIG. 5 wherein the bags 220 and 230 are located on the outside or exterior of the housing 122. In this configuration, openings are made in the housing 122 and the holes 222 and 232 of the bags are located just inside the housing 122 at these openings. The agents bead out of the holes 222 and 232 and are wicked off or dislodged by the flowing gas stream through the chamber 128. In addition, there will be a natural tendency for the agent in the bags 220 and 230 to enter the flowing gas stream from the holes 222 and 232 due to the change in vapor pressure. Because the gas stream is relatively dry and by contrast, the agent in the bags 220 and 230 may have some degree of moisture, a natural mechanism occurs by which the moist agent will wick out of the bags in an attempt to reach a vapor pressure equilibrium. The greater the rate of flow of the gas stream, the less of the agent in the bags 220 and 230 that will bead into the gas stream. The same theory of operation applies to the embodiment of FIG. 5.

Even if deployed on the outside of the housing 122, the bags 220 and 230 can be filled through their respective charging ports 224 and 234 in the same manner as described in conjunction with FIG. 5. The number of bags may vary on a particular application, and two are shown in FIGS. 5 and 6 only as an example. All other features concerning the heating, humidification and sensing in the housing 122 are applicable to the embodiments shown in FIGS. 5 and 6.

A still further variation on the embodiments of FIGS. 5 and 6 is to provide the optional tubing member 250 that extends from a bag to an optional absorbent pad 130 that is positioned within the housing 122.

Further embodiments for deploying one or more agents into the gas stream are shown in FIGS. 7 and 8. FIG. 7 shows an elongated tubing member 300 that is disposed in the chamber 128 of the housing 122. The tubing member 300 is extremely long and winds throughout the chamber 128; FIG. 7 is over-simplified in this respect. The tubing member 300 is, for example, a polyimide tubing product manufactured by MicroLumen of Tampa, Fla. The important characteristics of the tubing material are that the sides or walls of the tubing member 300 be as thin as possible so that the volume of agent that the tubing member 300 can carry is maximized. At the tip or end of the tubing member 300 is a restrictive orifice or hole 310 through which the agent may bead and be wicked off or dislodged into the gas stream in the chamber 128. If multiple types of agents are to be delivered into the gas stream, then multiple tubing members each containing a different agent is provided. A charging port 312 is also provided on the proximal end of the tubing member 300 just outside the housing 122 to supply a quantity of the agent into the tubing member 300.

FIG. 8 illustrates a variation of the embodiment shown in FIG. 7, wherein a tubing member 400 is provided that includes one or a plurality of holes or perforations 410 along the length of the tubing member 400 through which the agent is allowed to release into the chamber 128. The gas stream flowing through the chamber 128 will wick off or dislodge the agent from the holes 410 and carry the agent in the gas stream. The tubing member 400 has a charging port 412 similar to charging port 300 for tubing member 300. Also, multiple tubing members 400 may be provided in the chamber to release multiple types of agents into the gas stream. The length of each tubing member 400 and the quantity and size of the holes 412 therein may be selected to control the rate at which different agents from different tubing members 400 are wicked off or dislodged by the gas stream flowing through the chamber 128.

In the embodiments shown in FIGS. 2-8, the size of the chamber 128 of the gas treater housing 122 may vary depending on the intended use, gas flow, type of agent, whether and how many absorbent pads are provided, etc. There is no limit, either relative small, or relatively large, to the size of the chamber for purposes of carrying out the present invention.

Figure 9:
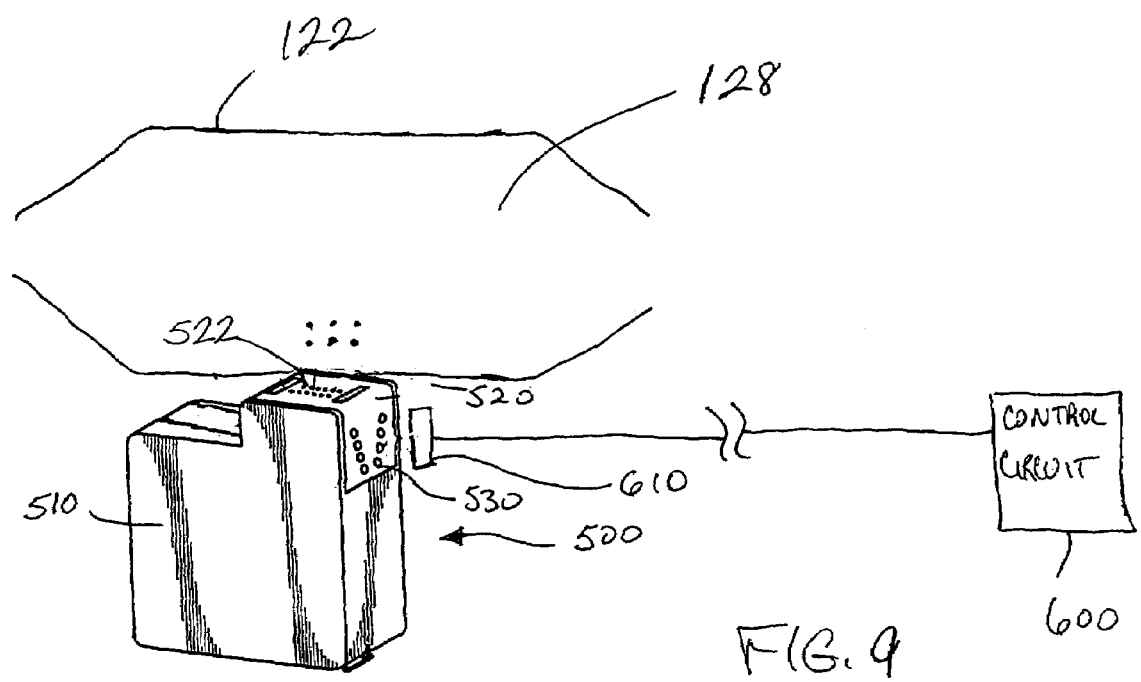
FIG. 9 is a schematic diagram of still another embodiment featuring an inkjet printhead for controllably releasing a quantity of one or more agents into the chamber of the gas treater housing.

Turning to FIG. 9, yet another embodiment is shown wherein an inkjet printhead cartridge 500 is used to release vapor bubbles containing a quantity of one or more agents into the chamber 128 of the housing 122. The inkjet printhead cartridge 500 may be one of any known inkjet printheads such as those used in inkjet printers sold by Hewlett-Packard, Canon, etc.

As is well known in the art, an inkjet printhead cartridge, such as that shown at reference numeral 500, comprises a reservoir 510, a printhead 520 and a plurality of contact pads 530. Conductive traces in the cartridge 500 are terminated by the contact pads 530. The contact pads are designed to normally interconnect with a printer so that the contact pads 530 contact printer electrodes that provide externally generated energization signals to the printhead 520 to spray ink onto paper. Thermal inkjet printheads create vapor bubbles by elevating the ink temperature, at the surface of a plurality of heaters, to a superheat limit. This same process can be used to create vapor bubbles of one or more agents. The printhead 520 comprises a plurality of nozzles 522 from which the vapor bubbles are released when heaters are energized to heat the quantity of agent contained in the reservoir.

According to the present invention, the inkjet printhead cartridge 500 is connected to a control circuit 600 by way of connector 610 having contacts to match the contact pads 530. The control circuit 600 may be contained within the control module 140 shown in FIG. 1 and coupled to the cartridge 500 by one or more electrical conductors contained in the electrical cable 170. The reservoir 510 is filled with a quantity or volume of one or more agents to be released into the chamber 128. For example, a color inkjet printhead cartridge contains multiple chambers or reservoirs for each of three colors of ink. Using this same type of device, an inkjet printhead cartridge may contain a quantity or volume of several different agents to be separately or simultaneously delivered into the chamber in controlled amounts. The control circuit 600 generates appropriate control signals that are coupled to the cartridge 500 via the connector 610 to drive the heaters in the printhead 520 and release vapor bubbles of one or more agents into the chamber from the nozzles 522.

When the one or more agents are released into the chamber 128, the gas stream that flows through the chamber and carries the agent out the exit port of the housing 122 and into the animal. Each of the different agents can be released into the chamber 128 at different rates or volumes. Furthermore, it is possible that a different inkjet printhead cartridge is provided for each of separate subchambers inside chamber 128 to keep the agents from mixing for a period of time before delivered into the animal.

Referring back to FIG. 2, electrical connections to the components inside the housing 122 of the gas treater 120 are as follows. A ground or reference lead (not specifically shown) is provided that is connected to each of the temperature sensor 136, heating element 134 and humidity sensor 138-timer/divider 145. A wire 175 (for a positive lead) electrically connects to the heating element 134 and a wire 176 (for a positive lead) electrically connects to the temperature sensor 136. In addition, three wires 177A, 177B and 177C electrically connect to the humidity sensor 138-timer divider circuitry, wherein wire 177A carries a DC voltage to the timer/divider 145, wire 177B carries an enable signal to the timer/divider 145, and wire 177C carries an output signal (data) from the timer/divider 145. All of the wires are fed from the insulated cable 170 into the feedthrough 174 and through small holes in the housing 122 into the chamber 128. The feedthrough 174 is sealed at the opening 178 around the cable 170.

The charging port 190 is attached to a lateral extension 139 of the housing 122. The charging port 190 comprises a cylindrical body 192 containing a resealable member 194. The resealable member 194 permits a syringe or similar device to be inserted therethrough, but seals around the exterior of the syringe tip. This allows a volume of liquid agent or humidifying solution to be delivered into the chamber 128 without releasing the liquid already contained therein. The resealable member 194 is, for example, Baxter InterLink™ injection site 2N3379. Alternatively, the charging port may be embodied by a one-way valve, a sealable port, a screw cap, a cap with a slit to permit the introduction of a syringe or other device, such as a Safeline™ injection site, part number NF9100, manufactured by B. Braun Medical Inc., or any other covering material or member capable of permitting the introduction of a syringe and preventing the backflow of contained liquid or gas. The control module 140 will issue a warning when the humidity of the gas being treated by the gas treater 120 drops below a predetermined or user programmable relative humidity, as explained hereinafter.

As an alternative, or in addition to the sensing and monitoring features described above, a backup or reserve supply container for liquid agent and/or humidifying solution is provided. Referring back to FIG. 1, one form of a backup supply container is a container 800 that hangs free of the apparatus 100 and is connected with an access tubing 810 to the charging port 190. The container 800 is, for example, a bag such as an intravenous fluid bag and the access tubing 810 is a intravenous type tubing.

Another form of a backup supply container is a container 850 that attaches to a portion of the apparatus 100. For example, the container 850 is a reservoir tube, bag, syringe or tank that is attached to the tubing segment 162 or is strapped or fastened to the tubing segment 162 close to the gas treater 120. Another alternative would be to strap or fasten it to the outside of the housing 122 of the gas treater 120. The container 850 is connected to an access tubing 860 that connects into the charging port 190, similar to access tubing 810 described above.

Access tubing 810 and 860 have a penetrating member (not shown) at their distal ends to penetrate the charging port 190 to gain access to the chamber 128 of the gas treater housing 122. Alternatively, instead of the access tubing 860, the container 850 has at the end proximate the charging port 190 a tip member similar to that of the syringe 200 to penetrate and directly couple to the charging port 190.

The containers 800 and 850 can be pre-charged or charged prior to use according to techniques well known in the art.

For example, container 850 has an injection site 862 to enable injection of liquid into the container 850.

Preferably, the access tubing 810 or 860 of the backup supply containers 800 and 850, respectively, (or the integral penetrating tip of the container 850) extend far enough through the charging port 190 so as to make contact with one of the layers 130-132 so that the liquid therein is wicked off onto one of the layers 130-132 due to capillary forces. Alternatively, the access tubing 810 or 860 (or integral penetrating tip of the container 850) stops short of one of the layers 130-132, and the pressure differential created by the flowing gas stream through the housing 122 will wick off the liquid agent and/or humidifying solution from the end of these members to contribute to the treatment of the gas.

With reference to FIG. 2, another variation is to provide an extension tube 870 that leads from the charging port 190 where the access tubing 810 or 860 (or the integral penetrating tip member of the container 850) terminates, to the treatment subchamber inside the chamber 128, i.e., to contact one or more of the layers 130-132. Liquid agent and/or humidifying solution is continuously wicked out from the end of the extension tube 870 onto one of the layers 130-132.

In either form of the backup supply container, the basic principle is the same. The backup supply container provides is coupled through the charging port 190 to the treatment subchamber inside the chamber 128 to constantly replenish the treatment subchamber, e.g., one or more of the layers 130, 131 or 132. Consequently, the treatment subchamber will have an initial amount of liquid agent and/or humidifying solution (pre-charged or charged prior to use) and a backup supply from the backup supply container is constantly supplied to the treatment subchamber to constantly replenish it as gas flows through the chamber. The overall time of sufficient gas humidification and/or treatment is thereby lengthened to a duration that is suitable for all or nearly all gas delivery applications. As a result, there is no need to be concerned about decreasing humidity of the gas delivered. The backup supply container acts a backup to provide gas humidification and/or treatment for an entire procedure. Therefore, some forms of the apparatus 100 need not include the humidity and temperature sensing and monitoring features, or the recharge alert, described herein. These features provide another type of backup that may be useful in certain applications, instead of, or in addition to the backup supply container.

The desirable width and diameter of the gas treater is dependent upon many factors, including the intended use, the rate of gas flow from the gas source and the pressure desired to be maintained, which is affected more by the diameter of chamber 128 than by its length. A person of ordinary skill in the art, given the teachings and examples herein, can readily determine suitable dimensions for chamber 128 without undue experimentation. It should also be noted, however, that upon activating the apparatus or changing the demand on the apparatus (e.g., flow rate or pressure), there is a lag time of only several tenths seconds for sensing the temperature of gas and adjusting the heating element to achieve the proper gas or desired temperature. Such a fast start-up time is extremely beneficial.

Figure 10:
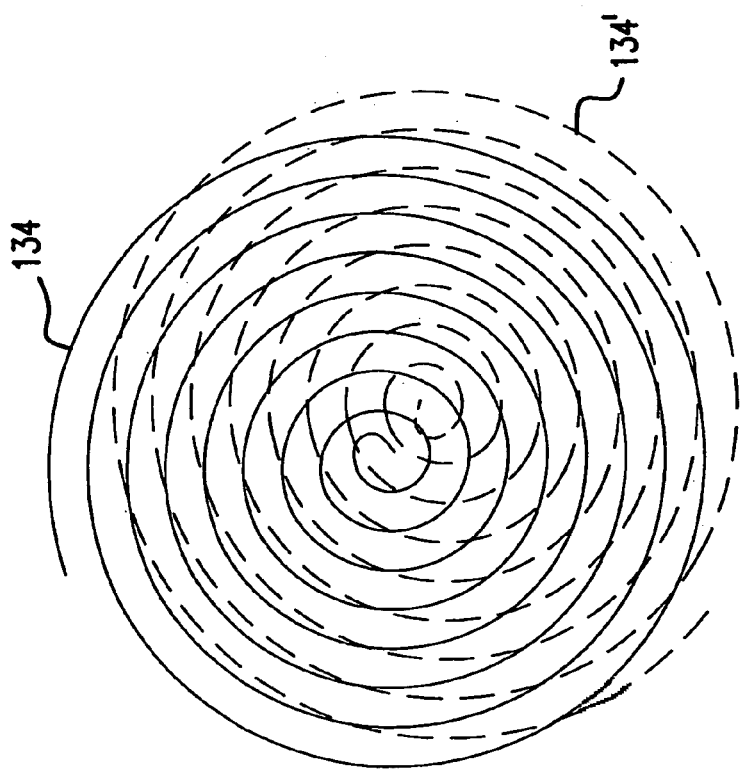
FIG. 10 is a schematic diagram of a heating element used in the gas treater.

Referring to FIG. 10, the heating element 134 is shown in more detail. The heating element 134 is an electrically resistive wire that is disposed in the housing 128 in a concentrical coil configuration having a number of turns, such as 6-8 turns. Alternatively, a second heating element 134' is provided that is arranged with respect to the heating element 134 such that its coils are offset from those of the first heating element, relative to the direction of gas flow through the chamber. If two or more heating elements are employed, they are preferably spaced from each other in the chamber of the gas treater by approximately 3-4 mm. The first and second heating elements 134 and 134' can be coiled in opposite directions relative to each other. This arrangement allows for maximum contact of the gas flowing through the chamber with a heating element. Other non-coiled configurations of the heating element 134 are also suitable.

Figure 11:
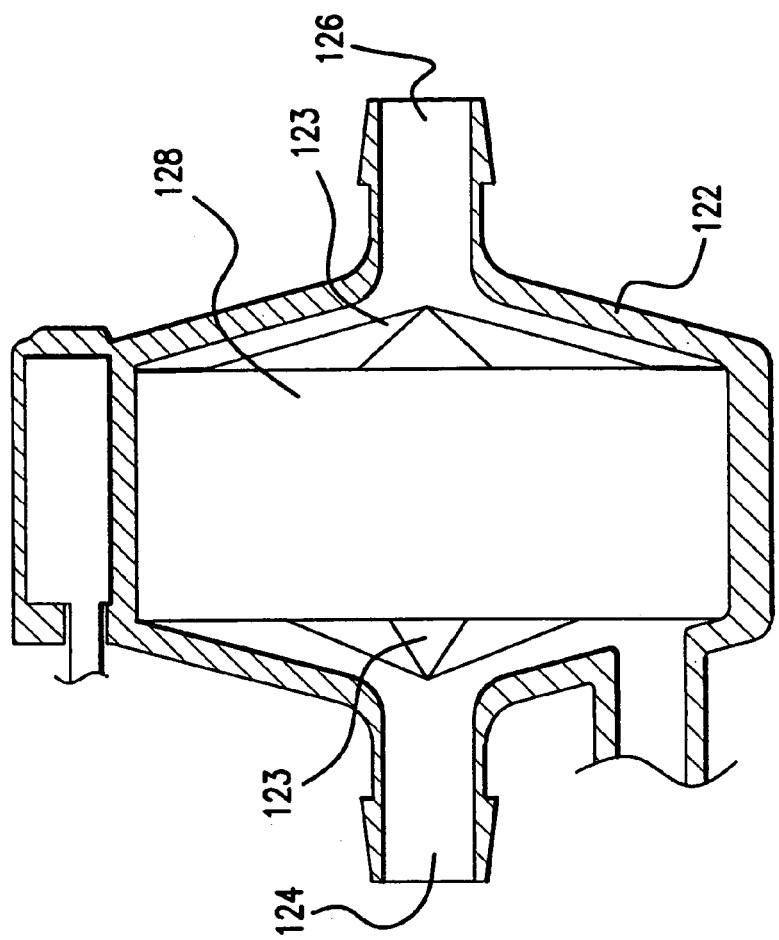
FIG. 11 is a cross-sectional view of the gas treater chamber and showing the fluted gas inlet and outlet of the chamber.

Turning to FIG. 11, another feature of the gas treater 120 is illustrated. At the inlet and/or outlet of the housing 122, fluted surfaces 123 may be provided to facilitate complete dispersion of gas as it is supplied to the gas treater 120. This improves the fluid dynamics of the gas flow through the chamber 128 to ensure that the gas is uniformly heated and humidified as it flows through the chamber 128.

FIGS. 12 and 13 illustrate embodiments of the apparatus to treat the gas stream with a solid phase agent. FIG. 12 shows a container 700 of a solid phase agent, such as in powder form, that is positioned in the chamber 128 of the gas treater housing 122. The container 700 includes a check valve 710 and a pressurizer 720, such as a carbon dioxide cartridge. When the pressurizer 720 is activated, pressure inside the container 700 is caused to rise, such that the bias of the check valve 710 is overcome, releasing the agent into the chamber 128. A button 730 on the exterior of the housing 122 is coupled by a wire or other means to the pressurizer 720 to activate it remotely.

FIG. 13 shows a container 700 of solid phase agent positioned outside of the housing 122. The check valve 710 of the container 700 is fed through an opening in the housing 122 into the chamber 128. The button 730 for activating the pressurizer is optionally positioned on the exterior of the container 700. Operation of the configuration shown in FIG. 13 is similar to that of FIG. 12.

In the embodiments of FIGS. 12 and 13, the rate at which the solid phase agent is released into the chamber 128 is dependent upon the pressure created in the container 700 by the pressurizer 720 and the size of the check valve 710. It may be desirable to deliver short bursts of the solid phase agent into the gas stream, or to deliver it into the gas stream on a continuous basis. If necessary, a separate backup source of pressure may be coupled to the container 700 to provide for longer term treatment of the gas stream. In any case, the gas stream flowing through the housing 122 will carry the solid phase agent with through the exit port.

Figure 14:
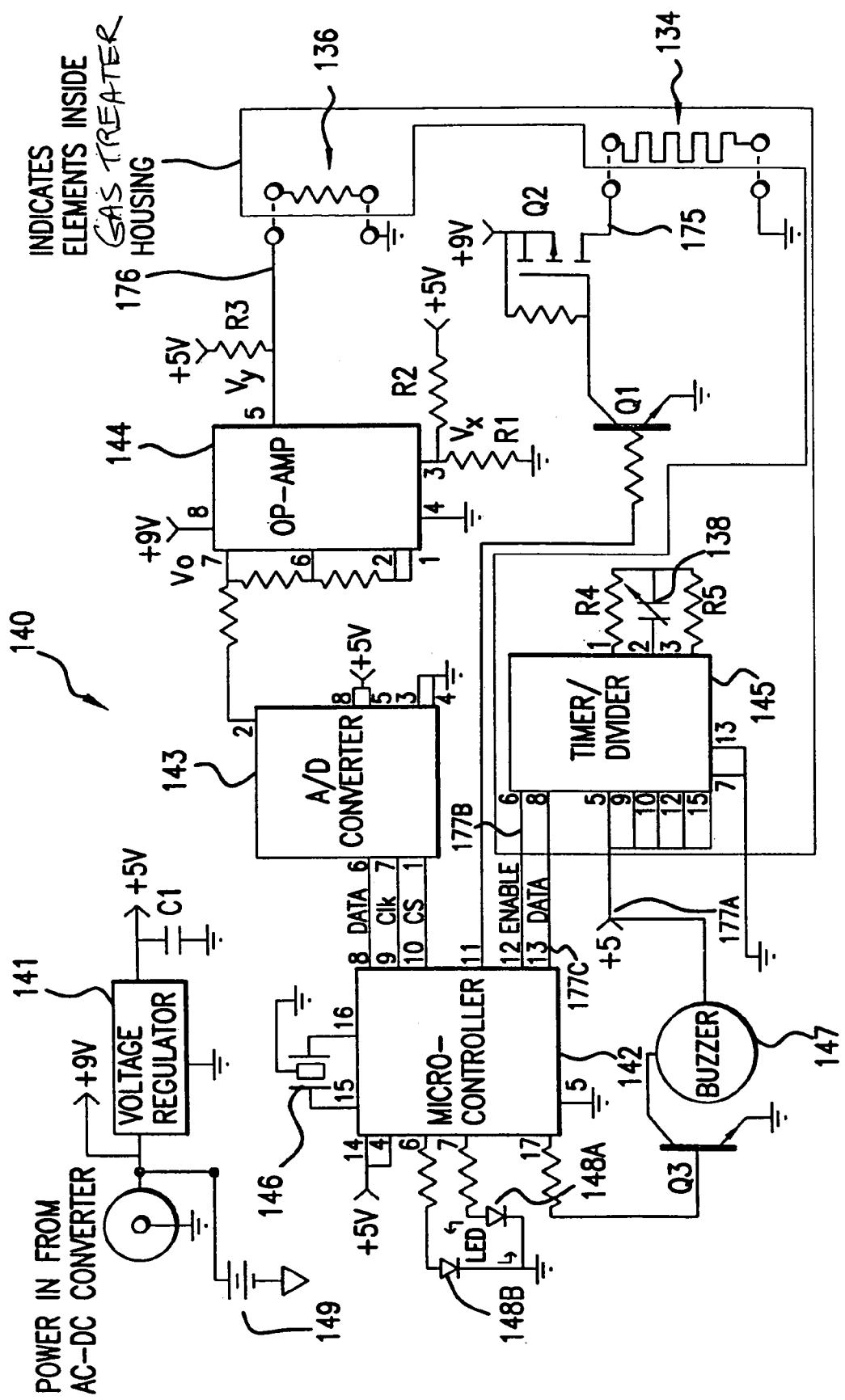
FIG. 14 is a schematic diagram showing a circuit for controlling the temperature of the gas and for monitoring the humidity of the gas.

Referring to FIG. 14, the control module 140 will be described in detail. The control module 140 contains monitoring circuitry and control circuitry for the apparatus 1100. It is understood that some forms of the apparatus 100 need not include the humidity (and heating) sensing, monitoring, temperature control and recharge alert functions. The control module 140 comprises a voltage regulator 141, a microcontroller 142, an A/D converter 143, a dual operational amplifier (hereinafter "op-amp") module 144, and a timer/divider 145. The monitoring circuit portion of the control module 140 consists of the combination of the microcontroller 142 and timer/divider 145. The control circuit portion of the control module 140 consists of the microcontroller 142, A/D converter 143 and op-amp module 144. The monitoring circuit monitors the relative humidity of gas exiting the chamber based on a signal generated by the timer/divider 145. The control circuit monitors the temperature of the gas exiting the chamber, and in response, controls electrical power to the heating element to regulate the temperature of the gas to a user, programmable or fixed temperature or temperature range. While the temperature of the gas exiting the chamber is actively controlled, the relative humidity of the gas in the chamber is not actively controlled; rather it is monitored and an alert is generated when it drops below a corresponding threshold so that appropriate action can be taken, such as replenishing the gas treater 120 with liquid agent or humidifying solution.

FIG. 14 shows that several components are preferably located within the electrical housing 210 (FIG. 1), whereas other components are located within the housing of the gas treater 120 (FIG. 2). In particular, the timer/divider 145 and the associated resistors R4 and R5 are preferably located inside the housing 122 of the gas treater 120, together with the humidity sensor 138 in a circuit package that includes the humidity sensor 138 exposed on one or more surfaces thereof. More specifically, the timer/divider 145 is co-located with humidity sensor 138. This configuration minimizes timing error by stray wiring inductance and capacitance (sensor kept close to active circuits of timer/divider 145). In addition, by co-locating the timer/divider 145 and humidity sensor 138, the need for interconnecting wires is eliminated, thereby avoiding undesirable signal radiation.

The voltage regulator 141 receives as input the DC output of the AC-DC converter 180 (FIG. 1), such as for example, 9 V DC, that is suitable for use by the analog components of the control module. The voltage regulator 141 regulates this voltage to generate a lower voltage, such as 5 V DC, for use by the digital components of the control module. The capacitor C1 at the output of the voltage regulator 141 serves to filter out any AC components, as is well known in the art. Alternatively, a suitable DC voltage is provided by a battery or photovoltaic source shown at reference numeral 149.

The microcontroller 142 may be a PIC16C84 integrated circuit microcontroller that controls system operation. A ceramic resonator 146 (4 MHZ) is provided to supply a raw clock signal to pins 15 and 16 of the microcontroller 142, which uses it to generate a clock signal for the signal processing functions explained hereinafter.

The op-amp 144 module is coupled (by wire 176) to the temperature sensor 136 (thermistor) mounted in the housing of the gas treater. The op-amp module 144 is, for example, a LTC1013 dual low-input-offset-voltage operational amplifier integrated circuit that includes two op-amps, referred to hereinafter as op-amp A and op-amp B. The non-inverting input of the op-amp A of the op amp module 144 is pin 3, and pin 2 is the inverting input. The output of op-amp A is pin 1. Op-amp A of the op-amp module 144 is used to buffer the output voltage of the voltage divider formed by resistors R1 and R2. The buffered output voltage, referred to as Vx in FIG. 14, is applied to op-amp B in the op-amp module 144. Op-amp B is configured as a non-inverting-with-offset amplifier with a gain of 21.5, and also receives as input the output of the temperature sensor 136, adjusted by resistor R3, shown as voltage Vy in the diagram. The output voltage of op-amp B is at pin 7, referred to as Vo in FIG. 14. The output voltage Vo is equal to 21.5Vy−20.5Vx, which is inversely proportional to the gas temperature in the housing of the gas treater. The output voltage Vo ranges between 0-5 V DC, depending on the temperature of the gas in the chamber.

The A/D converter 143 is an ADC 0831 integrated circuit analog-to-digital converter that receives as input at pin 2, the output Vo of the op-amp module 144. The A/D converter 143 generates a multi-bit digital word, consisting of 8 bits for example, that represents the output voltage Vo, and is supplied as output at pin 6, which in turn is coupled to I/O pin 8 of the microcontroller 142. The microcontroller 142 commands the A/D converter 143 to output the digital word by issuing a control signal on I/O pin 10 which is coupled to the chip select pin 1 of the A/D converter 143. Moreover, the microcontroller 142 controls the rate at which the A/D converter 143 outputs the digital word by supplying a sequence of pulses on pin 9 applied to clock input pin 7 of the A/D converter 143. The "unbalanced bridge" values of resistors R1, R2 and R3 are chosen to produce a 0-5 V DC output over gas temperatures from approximately 20° C. to approximately 45° C. Since the bridge and the reference for the A/D converter 143 are provided by the same 5 V DC source, error due to any reference voltage shift is eliminated.

The timer/divider 145 is, for example, a MC14541 precision timer/divider integrated circuit. The humidity sensor 138 is connected to pin 2 and to resistors R4 and R5 as shown. In response to an enable signal output by the microcontroller 142 on pin 12 that is coupled to timer/divider pin 6, the timer/divider 145 generates an output signal that oscillates at a rate determined by the value of the resistor R4, the capacitance of the humidity sensor 138 (which varies according to the relative humidity of the gas inside the gas treater housing) and a predetermined divider constant. For example, the divider constant is 256. Specifically, the output signal of the timer/divider 145 is a square wave oscillating between 0 V ("low") and 5V ("high") at a frequency of approximately $1/[256*2.3*R4_t*C_t]$ Hz, where R4 is, for example, 56 kOhms, and $C_t$ is the capacitance at some time (t) of the relative humidity sensor 138 depending on the relative humidity of the gas in the chamber. For example, the humidity sensor manufactured by Phillips Electronics, referred to above, can measure between 10-90% RH (relative humidity), where $C_t$ at 43% RH is 122 pF (+/−15%), with a sensitivity of 0.4+/−0.5 pF per 1% RH. The output signal of the timer/divider 145 appears at pin 8, which is coupled to the I/O pin 13 of the microcontroller 142. Thus, the timer/divider 145 is essentially an oscillator circuit connected to the humidity sensor that generates an output signal with a frequency dependent on a capacitance of the humidity sensor. Any oscillator circuit that can generate as output a signal whose frequency is dependent on a variable capacitance may be suitable for the timer/divider 145.

The microcontroller 142 computes a measure of the relative humidity of the gas inside the gas treater housing by timing or measuring a characteristic of the output signal of the timer/divider 145. Specifically, microcontroller measures the time duration of one of the phases of the output signal of the timer/divider 142, such as the "high" phase which is approximately $\frac{1}{2}*[256*2.3*R4_t*C_t]$. This time duration is indicative of the relative humidity of the gas in the chamber of the gas treater since the rate of the oscillation of the timer/divider depends on the capacitance of the humidity sensor 138, as explained above. For example, for a change in RH of 10-50% and/or 50 to 90%, there is a 13% change in the duration of the "high" phase of the timer/divider output signal. The microcontroller 142 monitors the relative humidity of the gas exiting the chamber in this manner and when it drops below a predetermined or user programmable relative humidity threshold (indicated by a corresponding predetermined change in the oscillation rate of the timer/divider 145), the microcontroller 142 generates a signal on pin 17, called a recharge signal, that drives transistor Q3 to activate an audible alarm device, such as buzzer 147. The buzzer 147 generates an audible sound which indicates that the relative humidity of the gas in the gas treater has dropped below the predetermined or user programmable threshold and that it is necessary to recharge the gas treater with liquid agent and/or humidifying solution. The relative humidity threshold corresponds to a minimum level for a desirable relative humidity range of the gas exiting the gas treater, and may be 40%, for example. The relative humidity threshold is an adjustable or programmable parameter in the microcontroller 142. Optionally, the microcontroller 142 may generate another warning signal at the output of pin 7 to illuminate an light emitting diode (LED) 148A, thereby providing a visual indication of the humidity dropping below the relative humidity threshold in the gas treater, and the need to recharge the gas treater 120 with liquid agent and/or humidifying solution. Further, the microcontroller 142 generates a trouble or warning signal output at pin 6 to drive LED 148B (of a different color than LED 148A, for example) when there is either a "code fault" in the microcontroller 142 (an extremely unlikely occurrence) or when the relative humidity of the gas in the gas treater is less than a critical relative humidity threshold (lower than the relative humidity threshold), such as 10%. In either case, power to the heating element 134 is terminated in response to the warning signal.

The microcontroller 142 also controls the heating element 134 in order to regulate the temperature of the gas inside the gas treater. Accordingly, the microcontroller 142 processes the digital word supplied by the A/D converter 143 to determine the temperature of the gas inside the gas treater housing. In response, the microcontroller 142 generates a heat control signal on the output pin 11 that drives transistor Q1, which in turn drives the MOSFET power transistor Q2, that supplies current to the heating element 134. The temperature of the gas inside the gas treater is regulated by the microcontroller 142 so that it is substantially at a predetermined or user programmable temperature or within a predetermined or user programmable temperature range as it exits the gas treater for delivery into the body of a animal. For laparoscopy procedures, the temperature range that the gas is regulated to be approximately 35°-40° C., but preferably is 37° C. when it exits the Luer lock 168. The control module 140 may include a rheostat or dial-type control to allow a user to adjust the desired temperature or temperature range of the gas that is delivered into the animal. As mentioned above, when the relative humidity inside the gas treater falls below a critical threshold as determined by the monitoring circuit portion of the control module 140, the control circuit portion in response terminates power to the heating element 134 to prevent the delivery of warm gas that is extremely dry.

The circuitry for monitoring the relative humidity of the gas can be embodied by other circuitry well known in the art. In addition, while the control module 140 has been described as having a single microcontroller 142 for monitoring signals representing temperature and relative humidity of the gas exiting the chamber, and for controlling the heating element to control the temperature of the gas, it should be understood that two or more microcontrollers could be used dedicated to the individual functions. In addition, the functions of the microcontroller 142 could be achieved by other circuits, such as an application specific integrated circuit (ASIC), digital logic circuits, a microprocessor, or a digital signal processor.

Figure 15:
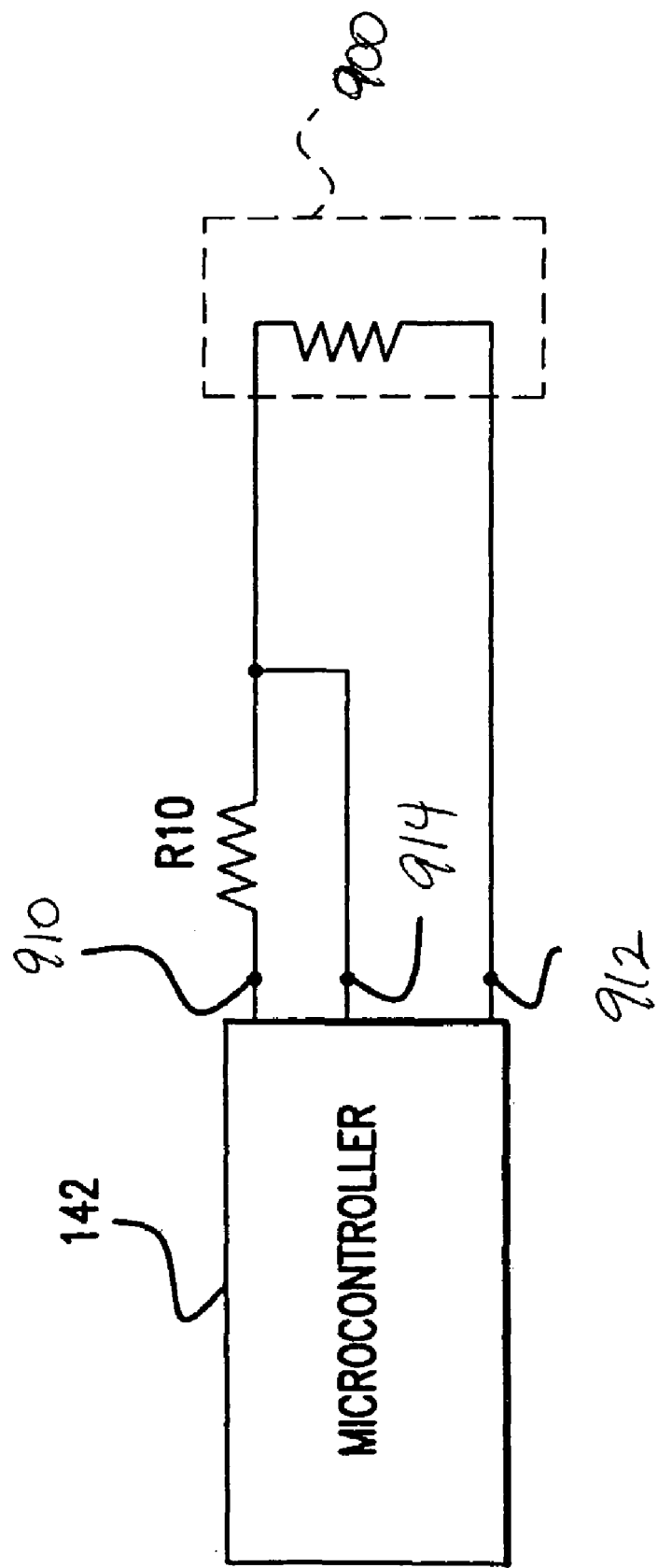
FIG. 15 is a schematic diagram showing a circuit for monitoring humidity of the gas according to an alternative embodiment.

FIG. 15 illustrates an alternative embodiment for monitoring relative humidity of the gas, in which a humidity sensitive resistor is used, instead of a humidity sensitive capacitor 138. The humidity sensing scheme employing a resistive humidity sensor does not require the timer/divider circuit 145 shown in FIG. 14. The humidity sensitive resistor 900 is located inside the gas treater housing in a suitable location for sensing the relative humidity of the gas stream flowing through the gas treater 120. A suitable humidity sensitive resistor is a model UPS600 resistor by Ohmic, which at 45% RH is approximately 30.7 kOhms. A resistor R10 is coupled in a voltage divider configuration with the humidity sensitive resistor 900. Three pins of the microcontroller 142 couple to the voltage divider formed by resistor R10 and humidity sensitive resistor 900.

Pin 910 of the microcontroller 142 is coupled to one terminal of the resistor R10, pin 912 is coupled to one terminal of the humidity sensitive resistor 900 and pin 914 is coupled to the terminal between the resistor R10 and the humidity sensitive resistor 900. The humidity sensitive resistor 900 may be a type that requires AC excitation. Accordingly, the microcontroller 142 excites the humidity sensitive resistor 900 by applying an alternating pulse, such as a 5 volt pulse, to pins 910 and 912, such that pin 910 is "high" (i.e., at 5 V) for a period of time and pin 912 is "low" (i.e., 0 V), then pin 912 is "high" for a period of time and pin 910 is low. As a result, the average excitation voltage to the humidity sensitive resistor 900 is zero. During the time period when pin 910 is "high", the microcontroller 142 senses the humidity of the gas by determining if the tap voltage pin 914 is a logic "zero" or a logic "one." If it is a logic zero (low voltage), the resistance of the humidity sensitive resistor 900 is low, indicating that the relative humidity of the gas is still high. If it is a logic one (high voltage), then the resistance of the humidity sensitive resistor 900 is high, indicating that the relative humidity of the gas is low. The value of the resistor R10 is chosen to yield a transition at pin 914 at a desired humidity threshold, such as 45% RH, with a 2.5 V transition from a low voltage to a high voltage. For example, resistor RIO is a 30 k Ohm resistor. In the embodiment employing a resistive humidity sensor, a microcontroller that is suitable is a PIC 16C558 in place of the microcontroller model referred to above in conjunction with FIG. 14. This sensing scheme can be simplified even further if a relative humidity sensor that allows DC excitation is used. In this case, only one pin of the microcontroller 142 need be associated with humidity sensing. A resistive humidity sensor has certain advantages over a capacitive humidity sensor. It has been found that the specific type of resistive humidity sensor referred to above can tolerate immersion in water in the gas treater 120 if a user accidentally over-fills the gas treater 120. In addition, the sensing scheme using a resistive sensor does not require a relatively high frequency square wave signal, which may be undesirable in some environments where the apparatus is used. Finally, the resistive sensor affords better accuracy for relative humidity sensing in some applications.

Other variations or enhancements to the circuitry shown in FIG. 14 are possible. The type of microcontroller used can be one, such as the PIC16C715, that incorporates the functions of the A/D converter 143. The PIC16C715 microcontroller incorporates a multi-channel A/D converter. In addition, a more feature rich microcontroller of this type will allow for the addition of a display, such as a liquid crystal display (LCD) or LED display. The microcontroller could generate information on a periodic basis to be displayed to the user, such as gas temperature and relative humidity. In addition, the microcontroller may directly drive an audible alert device, rather than indirectly driving it through a transistor as shown in FIG. 14. These are examples of the types of modifications or variations that are possible depending on the type of microcontroller that is selected for use in the control module 140.

With reference to FIGS. 1 and 2, the setup and operation of the apparatus 100 will be described. The AC/DC converter 180 is plugged into a 110V AC power source, such as a wall outlet or a power strip. The control module 140 is connected to the AC/DC converter 180. Alternatively, the apparatus 100 may be powered by a battery or photovoltaic source. The tubing set is then installed by attaching one end of the tube segment 160 to the outlet of the gas regulator 10 by the Luer lock 166. The tube segments 160, 162 and 164 may be pre-attached to the filter 110 and the gas treater 120 for commercial distribution of the apparatus 100. The cable 170 is installed into the electrical housing 210 of control module 140 by the connector 172.

The gas treater 120 is charged with a supply of liquid agent and/or humidifying solution by the syringe 200. The syringe 200 is then inserted into the charging port 190 so that a needle or cannula of the syringe 200 penetrates the resealable member 194 (FIG. 2) and the liquid agent and/or humidifying solution is injected into the gas treater 120 to be absorbed by the absorbent layers. The syringe 200 is then removed from the charging port 190, and the charging port 190 seals itself. The free end of the tube segment 164 is attached to a gas delivery device by the Luer lock 168 or other appropriate connector. Alternatively, the gas treater 120 may be pre-charged with the liquid agent and/or humidifying solution, thus not requiring a charge prior to operation.

Figure 8:
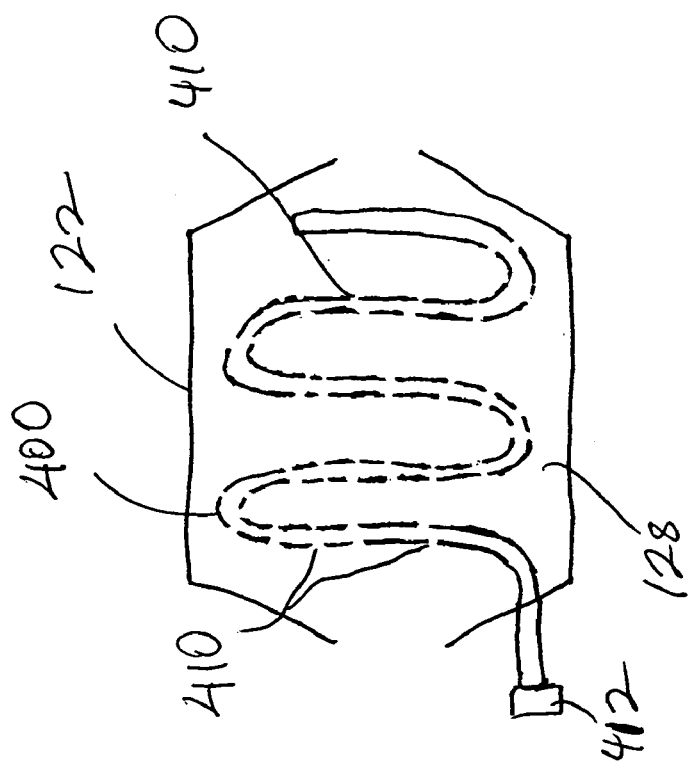
FIG. 8 is an internal view of the gas treater housing according to another embodiment featuring a tube member disposed within the housing and having a plurality of openings on a length portion thereof.
Figure 7:
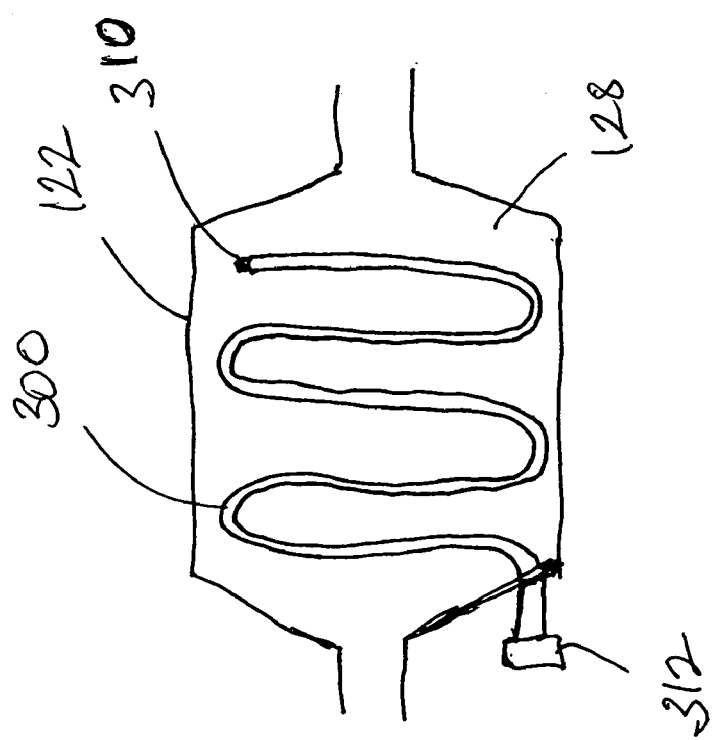
FIG. 7 is an internal view of the gas treater housing according to yet another embodiment featuring a tube member disposed within the housing and having a restrictive opening at a distal end thereof.

If the embodiment of FIG. 5 or 6 is employed, then the bags 220 and 230 are charged (unless they are pre-charged) with a quantity of one or more agents. Likewise, if the embodiment of FIG. 7 or 8 is employed, the tube member 300 or tube member 400 is charged (unless it is pre-charged) with a quantity of one or more agents. If the embodiment of FIG. 9 is employed, the reservoir(s) of the inkjet printhead cartridge 500 is charged (unless it is pre-charged) with a quantity of one or more agents. The nozzles 522 of the printhead 520 are positioned in alignment with an opening to the housing 122. Finally, if the embodiment of FIG. 12 or 13 is employed, the container 700 is prepared for use as described above in conjunction with FIGS. 12 and 13.

Once the gas regulator 10 is activated, it receives gas from a gas supply cylinder and regulates the pressure and flow rate of the gas, both of which can be adjusted by the operator. The pressure and volumetric flow rate are controlled by adjusting controls (not shown) on the gas regulator 10. Gas then flows through the tube segment 160 into the optional filter 110 where it is filtered, and then through tube segment 162 into the gas treater 120. In the gas treater 120, gas comes into contact with the optional electrical heating element 134 and the optional humidifying liquid-retaining layer(s) 130-132 which are positioned within the flow path of the gas, as shown in FIG. 2.

Depending on which gas treater embodiment of FIGS. 2-9, 12 or 13 is employed, the gas stream is treated with a quantity of one or more agents so that the one or more agents is carried out of the gas treater 120 for delivery to an animal. For some applications and temperature range requirements, it may be desirable to position the gas treater 120 immediately adjacent the location to which the treated gas is to be delivered.

In the event that heating and humidification of the gas is also desired and the appropriate components are also deployed in the gas treater 120, then in chamber 128, the gas is also simultaneously heated and humidified to the proper physiological range by regulation of the heating element 134 and liquid content of the layers 130-132 such that the temperature of gas exiting chamber 128 is within a preselected physiological temperature range (preferably 35° to 40° C., though any desired temperature range can be preselected), and within a preselected range of relative humidity (preferably above 40% relative humidity, such as in the range of 80-95% relative humidity). If the apparatus is operated with the gas treater 120 not charged with liquid agent and/or humidifying solution either because the user forgot to manually charge it before initiating operation, or the apparatus was sold without a pre-charge of liquid (i.e., in a dry state), the relative humidity of the gas in the chamber of the gas treater 120 will be detected to be below the predetermined threshold and the alarm will be activated, alerting the user that the gas treater 120 requires charging, if a wet type of treatment is desired. The apparatus will automatically issue an alarm to alert a user to the need for charging the gas treater 120 with liquid agent and/or humidifying solution, thereby avoiding further delivery of unhydrated gas into a animal.

With further reference to FIG. 5, the control module 140 monitors the relative humidity of the gas exiting the chamber and further regulates the temperature of the gas in the chamber 128. In particular, the microcdntroller 142 generates a recharge signal when the relative humidity of the gas in the chamber drops below the predetermined relative humidity threshold, indicating that the liquid supply in the gas treater 120 requires replenishing. An audible alarm is issued by the buzzer 147 and/or a visual alarm is issued by LED 148A to warn the attendant or user that the gas treater 120 requires recharging. Preferably, the microcontroller 142 continues the alarm until the humidity in the chamber returns to a level above the predetermined relative humidity threshold, which will occur when the gas treater 120 is recharged with liquid. Moreover, the microcontroller 142 will issue a second alarm, such as by energizing LED 148B, when the relative humidity level of gas in the gas treater 120 drops below the critical relative humidity threshold, at which point electrical power to the heating element 134 is terminated. In addition, the microcontroller 142 controls the temperature of the gas by controlling electrical power supplied to the heating element 134.

In some cases, the controlled humidity of the gas stream is more important than controlled heating. For those applications, the apparatus would include only those components necessary to treat the gas stream with one or more agents (according to the embodiments of FIGS. 7-13) and to humidify the gas stream. Furthermore, monitoring the humidity of the gas stream is also optional for certain applications. For example, treating the gas stream with a dry agent may not normally require heating or humidification.

The method and apparatus of this invention can be utilized for any circumstances, including procedures requiring the treatment of gas with one or more agents, and the optional humidification and heating of the gas. The optional filtration may also be utilized according to the sterility of gas required for the procedure. Preferable gases for endoscopy are carbon dioxide and nitrous oxide. A combination of the above gases can also be used, i.e., 100% of a single gas need not be used. The procedure is preferably endoscopy such as laparoscopy, colonoscopy, gastroscopy, bronchoscopy, and thoracoscopy. However, it may also be utilized for providing heated and humidified oxygen or any anesthetic gases or combination of gases for breathing, for example, or to administer anesthesia or breathing therapy. In particular, the compact size of the apparatus make the invention portable and thus suitable for uses requiring portability. The gas delivery device that provides the direct contact to the animal should be selected according to the procedure to be performed as known to those skilled in the art. The gas that is conditioned by the apparatus may be pressure controlled, volumetrically controlled or both.

Throughout this application, various patents publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. An apparatus for treating gas with at least one agent, the gas being received into the apparatus from a gas source, the apparatus comprising:
   a) a housing having an inlet and an outlet;
   b) a single chamber within said housing having an entry port and an exit port, the entry port for connection to a laparoscopic insufflator to receive there from a gas stream; and the exit port for exit of the gas stream from the single chamber; and
   c) a first quantity of a pharmacologic agent contained within the chamber and positioned such that a portion of the pharmacologic agent may be admixed with and carried by the gas stream through the exit port.

2. The apparatus defined in claim 1, and further comprising a container containing a second quantity of the pharmacologic agent, the container in fluid communication with the chamber.

3. The apparatus defined in claim 2, wherein the container comprises a port to receive a quantity of an agent.

4. The apparatus defined in claim 1, and further comprising at least one layer of an absorbent material positioned inside the chamber to absorb a quantity of the pharmacologic agent.

5. The apparatus defined in claim 1, and further comprising:
   a) a back-up or reserve supply container; and
   b) an access tubing connecting said back up or reserve container to a charging port in fluid communication with the single chamber.

6. The apparatus defined in claim 5, wherein the backup or reserve supply container is attached to a portion of the apparatus.

7. The apparatus defined in claim 5, wherein the backup or reserve supply container hangs free of the apparatus.

8. The apparatus defined in claim 1, and further comprising a humidity sensor positioned in the single chamber in the flow path of the gas stream.

9. The apparatus defined in claim 1, and further comprising a heating element disposed within the chamber.

10. The apparatus defined in claim 9, and further comprising:
    a) a temperature sensor disposed within the chamber.

11. An apparatus for treating gas with a humidifying solution and at least one pharmacologic agent, the gas being received into the apparatus from a gas source, the apparatus comprising:
    a) a housing having an inlet and an outlet;
    b) a single chamber within said housing having an entry port communicating with the inlet of the housing and an exit port communicating with the outlet of the housing, the entry port for connection to a laparoscopic insufflator to receive there from a gas stream;
    c) a first quantity of the humidifying solution contained within the single chamber and positioned such that a portion of the humidifying solution may be admixed with and carried by the gas stream through the exit port;
    d) a first quantity of a pharmacologic agent contained within the single chamber and positioned such that a portion of the pharmacologic agent may be admixed with and carried by the gas stream through the exit port; and
    e) a backup or reserve supply container for the pharmacologic agent and/or humidifying solution in fluid communication with said chamber.

12. The apparatus defined in claim 11, and further comprising at least one container for containing a quantity of the humidifying solution and a quantity of the pharmacologic agent, the at least one container in fluid communication with the single chamber.

13. The apparatus defined in claim 12, wherein the at least one container comprises a port to receive at least some of either or both of the humidifying solution or the pharmacologic agent.

14. The apparatus defined in claim 11, and further comprising at least one layer of an absorbent material positioned inside the chamber to absorb at least a portion of the first quantity of the pharmacologic agent.

15. The apparatus defined in claim 11, and further comprising an access tubing connecting the backup or reserve supply container to a charging port in fluid communication with the single chamber.

16. The apparatus defined in claim 11, wherein the backup or reserve supply container hangs free of the apparatus.

17. The apparatus defined in claim 11, wherein the backup or reserve supply container is attached to a portion of the apparatus.

18. The apparatus defined in claim 11, and further comprising a humidity sensor positioned in the single chamber in the flow path of the gas stream.

19. The apparatus defined in claim 11, and further comprising a heating element disposed within the single chamber.

20. The apparatus defined in claim 19, and further comprising:
    a) a temperature sensor disposed within the single chamber.

21. An apparatus for treating carbon dioxide gas with at least one pharmacologic agent, the gas being received into the apparatus from a gas source, the apparatus comprising:
    a) a housing having an inlet and an outlet; and
    b) at least a single chamber within said housing having an entry port and an exit port, the entry port for connection to a laparoscopic insufflator to receive there from a carbon dioxide gas stream; the single chamber receiving a first quantity of a pharmacologic agent to be admixed with and carried by the carbon dioxide gas stream, the exit port for exit of the carbon dioxide gas stream from the single chamber.

22. The apparatus defined in claim 21, and further comprising a container containing a second quantity of the pharmacologic agent, the container in fluid communication with the chamber.

23. The apparatus defined in claim 21, wherein the at least one single chamber is a single chamber within said housing having an entry port communicating with the inlet of the housing, and an exit port communicating with the outlet of the housing, the entry port for connection to the laparoscopic insufflator to receive there from the carbon dioxide gas stream; said chamber receiving a quantity of a humidifying solution and a quantity of the at least one pharmacologic agent; and a backup or reserve supply container for the at least one pharmacologic agent.

24. An apparatus for treating gas with at least one agent, the gas being received into the apparatus from a gas source, the apparatus comprising:
   a) a housing having an inlet and an outlet;
   b) a single chamber within said housing having an entry port and an exit port, the entry port for connection to a laparoscopic insufflator to receive there from a gas stream; and the exit port for removal of the gas stream from the single chamber; and
   c) a quantity of the at least one agent contained within the chamber to be admixed with and carried by the gas stream for delivery to the peritoneum of a patient undergoing surgery.

25. An apparatus for treating gas with at least one agent, the gas being received into the apparatus from a gas source, the apparatus comprising:
   a) a housing having an inlet and an outlet;
   b) a single chamber within said housing having an entry port and an exit port, the entry port for connection to a laparoscopic insufflator to receive there from a gas stream; and the exit port for exit of the gas stream from the single chamber; and
   c) a first quantity of a solid phase pharmacologic agent introduced within the single chamber and positioned such that a portion of the solid phase pharmacologic agent may he admixed with and carried by the gas stream through the exit port.

26. The apparatus defined in claim 25, where the solid phase agent is a fume or a dust.

27. An apparatus for treating a gas with at least one agent, the gas being received into the apparatus from a gas source, the apparatus comprising:
   a) a housing having an inlet and an outlet;
   b) a single chamber within said housing having an entry port and an exit port, the entry port for connection to a laparoscopic insufflator to receive there from a gas stream; and the exit port for exit of the gas stream from the single chamber; and
   c) a quantity of a liquid phase pharmacologic agent contained within the single chamber and positioned such that a portion of the liquid phase pharmacologic agent may be admixed and carried by the gas stream through the exit port.

28. The apparatus defined in claim 27, wherein the liquid phase agent is a mist or a spray.

29. The apparatus defined in claim 27, wherein the liquid phase agent is wicked off or dislodged from a container.

* * * * *